United States Patent
Simm et al.

(10) Patent No.: US 10,713,572 B2
(45) Date of Patent: Jul. 14, 2020

(54) DATA DISCOVERY NODES

(71) Applicant: FlowJo, LLC, Ashland, OR (US)

(72) Inventors: Maciej Simm, Ashland, OR (US); Jay Almarode, Lebanon, OR (US); Michael D. Stadnisky, Ashland, OR (US)

(73) Assignee: FlowJo, LLC, Ashland, OR (US)

( * ) Notice: Subject to any disclaimer, the term of this patent is extended or adjusted under 35 U.S.C. 154(b) by 1073 days.

(21) Appl. No.: 15/150,095

(22) Filed: May 9, 2016

(65) Prior Publication Data

US 2016/0328649 A1    Nov. 10, 2016

Related U.S. Application Data

(60) Provisional application No. 62/158,903, filed on May 8, 2015.

(51) Int. Cl.
| | | |
|---|---|---|
| G06N 5/02 | (2006.01) | |
| G06N 5/00 | (2006.01) | |
| G06F 16/16 | (2019.01) | |
| G16B 50/00 | (2019.01) | |
| H04L 29/08 | (2006.01) | |

(Continued)

(52) U.S. Cl.
CPC ......... *G06N 5/022* (2013.01); *G06F 9/44526* (2013.01); *G06F 16/164* (2019.01); *G06N 5/003* (2013.01); *G16B 50/00* (2019.02); *H04L 63/102* (2013.01); *H04L 67/10* (2013.01);

(Continued)

(58) Field of Classification Search
CPC ......... G01N 35/00603; G01N 15/1404; G01N 35/00; G06F 19/24; G06F 17/3051
See application file for complete search history.

(56) References Cited

U.S. PATENT DOCUMENTS 6,108,670 A * 8/2000 Weida ................... G06N 5/022
7,979,245 B1 * 7/2011 Bourlatchkov ..... G06F 11/3409
703/2

(Continued)

OTHER PUBLICATIONS

Gray, J. et al. (2010). "OpenMDAO: An open source framework for multidisciplinary analysis and optimization." 13th AIAA/ISSMO Multidisciplinary Analysis Optimization Conference. 2010. (Year: 2010).*

(Continued)

*Primary Examiner* — Kamran Afshar
*Assistant Examiner* — Benjamin J Buss
(74) *Attorney, Agent, or Firm* — Knobbe, Martens, Olson & Bear, LLP

(57) ABSTRACT

A framework and interface for invoking and assimilating external algorithms and interacting with said algorithms in-session and real-time are described herein. An example embodiment also includes reproducible, updatable nodes that can be leveraged for data-driven analysis whereby the data itself can direct the algorithm choice, variables, and presentation leading to iteration and optimization in an analysis workflow. With example embodiments, an entire discovery or diagnosis process may be executed on a particular data set, thereby divorcing the discovery or diagnosis process from a specific data set such that the same discovery or diagnosis process, phenotype identification, and visualizations may be repeated on future experiments, published, validated, or shared with another investigator.

24 Claims, 14 Drawing Sheets

(51) Int. Cl.
*G06F 9/445* (2018.01)
*H04L 29/06* (2006.01)
(52) U.S. Cl.
CPC .......... *H04L 67/141* (2013.01); *H04L 67/143* (2013.01); *H04L 67/20* (2013.01)

(56) References Cited

U.S. PATENT DOCUMENTS

| | | | |
|---|---|---|---|
| 8,078,749 B2* | 12/2011 | Khosravy | G06F 16/27 709/231 |
| 2002/0049782 A1 | 4/2002 | Herzenberg | |
| 2002/0150966 A1 | 10/2002 | Muraca | |
| 2002/0188217 A1 | 12/2002 | Farwell | |
| 2004/0049481 A1 | 3/2004 | Blevins | |
| 2004/0073463 A1 | 4/2004 | Helms | |
| 2005/0038608 A1 | 2/2005 | Chandra et al. | |
| 2005/0244955 A1 | 11/2005 | Li | |
| 2007/0016373 A1 | 1/2007 | Hunter | |
| 2007/0112652 A1 | 5/2007 | Ricketts | |
| 2007/0299799 A1 | 12/2007 | Meehan | |
| 2008/0010044 A1* | 1/2008 | Ruetsch | G06N 5/003 703/2 |
| 2009/0117555 A1 | 5/2009 | Kuypers | |
| 2009/0204557 A1 | 8/2009 | Zhang | |
| 2010/0053211 A1 | 3/2010 | Ingermanson | |
| 2010/0161561 A1 | 6/2010 | Moore | |
| 2010/0192084 A1 | 7/2010 | Ingermanson et al. | |
| 2010/0229150 A1 | 9/2010 | Stone | |
| 2011/0066385 A1 | 3/2011 | Rajwa et al. | |
| 2012/0050850 A1 | 3/2012 | Yamamoto | |
| 2012/0083454 A1 | 4/2012 | Vescovi | |
| 2012/0117533 A1 | 5/2012 | Hatcherson | |
| 2012/0159145 A1 | 6/2012 | Cheong | |
| 2012/0215481 A1* | 8/2012 | Covey | G01N 15/1404 702/123 |
| 2013/0006976 A1* | 1/2013 | Megler | G06F 16/248 707/725 |
| 2013/0103211 A1 | 4/2013 | Peterson | |
| 2013/0218845 A1 | 8/2013 | Kleppner | |
| 2014/0095504 A1 | 4/2014 | Soroushian | |
| 2014/0206559 A1 | 7/2014 | Whitesides | |
| 2014/0310635 A1 | 10/2014 | Lett | |
| 2014/0365191 A1* | 12/2014 | Zyglowicz | G06F 17/5009 703/7 |
| 2015/0111539 A1 | 4/2015 | Shim | |
| 2016/0170980 A1 | 6/2016 | Stadnisky et al. | |
| 2016/0328249 A1 | 11/2016 | Simm et al. | |
| 2016/0328516 A1 | 11/2016 | Simm et al. | |
| 2016/0328649 A1* | 11/2016 | Simm | G06N 5/022 |

OTHER PUBLICATIONS

Bischl, B. et al. (2012). "Algorithm Selection Based on Exploratory Landscape Analysis and Cost-Sensitive Learning". GECCO'12, Jul. 7-11, 2012, Philadelphia, Pennsylvania, USA. (Year: 2012).*

Mitkas, P. (2005). "Knowledge discovery for training intelligent agents: methodology, tools and applications." International Workshop on Autonomous Intelligent Systems: Agents and Data Mining. Springer, Berlin, Heidelberg, 2005. (Year: 2005).*

Azad, May 2014, An algorithmic pipeline for analyzing multi-parametric flow cytometry data, Ph.D. dissertation, Purdue University, 170 pp.

Frelinger et al., Jun. 17, 2008, Flow: statistics, visualization and informatics for flow cytometry, Source Code for Biology and Medicine, 3(1), 12 pp.

International Search Report and Written Opinion dated Dec. 19, 2016 in International application No. PCT/US206/031516.

Extended European Search Report dated Nov. 26, 2018 in European patent application No. 16793334.0.

* cited by examiner

Example Workspace XML
Encapsulated data sources, analysis, results, visualizations, and plugin inputs

```
<Workspace>
    <Groups>
        ... analysis
    </Groups>
    <SampleList>
        <Sample>
            ... data source reference
            <Population>
                ... analysis results
                <Plugin>
                    ... plugin inputs
                </Plugin>
            </Population>
        </Sample>
    </SampleList>
    <TableEditor>
        ... tabular report generation
    </TableEditor>
    <LayoutEditor>
        ... visualizations and batch generation specifications
    </LayoutEditor>
</Workspace>
```

Figure 2B

Example Plugin XML
Plugins save all inputs need to perform their work

E.g. DownSample
```
<Sample>
  <SampleNode>
    <Subpopulation>
      <ExternalPopNode>
        <DownSample numEvents="8000" version="1.0"/>
```

E.g. TSNE
```
<Sample>
  <SampleNode>
    <Subpopulation>
      <ExternalPopNode>
        <TSne version="1.0"/>
          <Option NumberOfIterations="1000"/>
          <Option Perplexity="20"/>
          ...
          <Parameter name="Rh103di"/>
          <Parameter name="Xe131Di"/>
          ...
```

Figure 2C

Knowledge base contains:

1. sample information sample metadata
Date:10-OCT-2008
System:Windows XP 5.1
Cytometer:LSRII
File:81.fcs
File URL:file:/Users/mikestadnisky/Deskto
--------------------
$BEGINDATA: 3584
$BEGINSTEXT: 0
$BTIM: 11:52:08
$BYTEORD: 4,3,2,1
$CYT: LSRII
$DATATYPE: F
$DATE: 10-OCT-2008
$ENDDATA: 2231503
$ENDSTEXT: 0
$ETIM: 11:52:32
$FIL: 81.fcs including parameters:
FSC-A
FSC-H
FSC-W
SSC-A
SSC-H
SSC-W
Time
Comp-FITC_Alexa 488-A :: CD56
Comp-PE-A :: CD11c
Comp-PE-Cy55-A :: CD3
Comp-CD3 CD14 Live_Dead-A :: 7AAD
Comp-APC_Ax 647-A :: 2H2
Comp-APC-Ax700-A :: CD4
Comp-APC-H7-A :: CD8

2. DDN execution parameters hierarchy (order) of analysis, analysis algorithm, parameters 3. biological result information – reference statistics

Figure 8C

DATA DISCOVERY NODES

CROSS-REFERENCE AND PRIORITY CLAIM TO RELATED PATENT APPLICATIONS

This patent application claims priority to U.S. provisional patent application Ser. No. 62/158,903, entitled "Data Discovery Nodes", filed May 8, 2015, the entire disclosure of which is incorporated herein by reference.

This patent application is related to (1) U.S. patent application Ser. No. 15/150,106, entitled "Plugin Interface and Framework for Integrating External Algorithms with Sample Data Analysis Software", filed May 9, 2016, and issued as U.S. Pat. No. 10,438,120 on Oct. 8, 2019, and (2) U.S. patent application Ser. No. 15/150,125, entitled "Plugin Interface and Framework for Integrating a Remote Server with Sample Data Analysis Software", filed May 9, 2016, the the entire disclosures of each of which are incorporated herein by reference.

INTRODUCTION

Due to improvements in technology, single cell experimentation instruments are able to generate far more information than previous instrument generations. For example, a flow cytometer may generate data representing many thousands of individual cells, with numerous parameters for each cell (e.g. 10 or more parameters). Consequently, the number of phenotypes that may be potentially identified has exponentially increased. In other words, the informational content produced by single cell assays has increased substantially prior to the filing of the present application. In addition, single cell inquisition has expanded to include the interrogation of many thousands of transcripts (RNA) molecules per cell and DNA modifications. For example, a whole transcriptome analysis will examine 10,000 genes at one time.

While generating more data provides more insight into the way cell phenotypes interact with each other or influence disease and their potential to express other disease-related proteins, the sheer amount of data generated by an acquisition instrument can be staggering and can overwhelm even the foremost of experts. Generally, life scientists focus their expertise on a set or sub-set of cell functions or cell phenotypes. For example, an immunologist focuses his or her practice on a handful of cell phenotypes to understand disease or immune cell function. Meanwhile, a systems-biologist may have a wealth of knowledge in cell interaction and the pathways which link genes and proteins together. It is unrealistic to expect an individual to be an expert in all cell populations because cellular interactions, identification, and functionality comprise a diverse and complex range of properties. Because a life scientist's expertise is generally limited to some, but not all, cell phenotypes (usually fewer than 50% of all currently known cell phenotypes), a knowledge discordance is created in discovery and diagnostic analysis because an expert does not intimately know how each cell phenotype correlates to disease or cellular interaction. As a result of this knowledge discordance, an expert may focus his study of data acquired by acquisition instruments on cell phenotypes known strongly by the expert. In limiting experiments and studies to a subset of phenotypes, an analyst may ignore or miss important phenotypes that could have a very big impact on disease or cell function. Furthermore, by focusing on known phenotypes, large amounts of data collected by the acquisition instrument may lay dormant and unused.

Analyzing a subset of data based on a subset of cell phenotypes may lead to interesting findings within experiments. However, cell responses may comprise cells expressing a pattern of multiple functions, and by analyzing only a subset of cell phenotypes, a scientist may fail to recognize how other cell populations impact a cellular response or disease. For example, an investigator may be conducting an experiment looking for a subset of T-cells that is important in a particular immune response. In this example, the subset of T-cells may be defined by a combination of four parameters (also known as markers). Of course, at the outset of the experiment, the investigator is not aware of the number of markers necessary to identify the subset of T-cells of interest. Thus, by examining more markers on more cells, an investigator may discover the cell subsets that correlate with morbidity or therapeutic efficacy, and, with more data analysis technology, an investigator may overcome his own knowledge discordance to find new and unexpected subsets that are important in disease or cellular function. Thus, there exists a need in the art for technology that compensates for a knowledge gap exhibited by most investigators and scientists.

The inventors believe that conventional technology solutions do not adequately bridge the gap between a scientist's lack of knowledge and actual cellular response. For example, while conventional technology may assist in an investigator's experiment by providing valuable analysis tools, those tools are still not enough to bridge the data-knowledge discordance. In a conventional discovery solution, an analyst must still perform manual clustering and apply analysis to a group of samples. However, in an example experiment having nine markers for examining cell phenotype, eight markers examining memory state, and eight markers examining cell signaling, the number of possible clusters is $2^{25}$ or 33,554,432 clusters, which are far too many clusters for manual analysis. In other words, the number of potential phenotypes and possible two-dimensional displays do not scale well with manual analysis. Of course, some phenotype pruning could occur to limit the phenotype space down to a more manageable number. For example, a life scientist could perform pre-process gating for single cells and live, intact cells with further phenotype pruning to examine CD3+CD45+/−/HLA-DR-/CD16+, CD4+, and CD8+ cells, which are further divided into Naïve, Effector, Central Memory, and Effector Memory cells. However, even in this phenotype-pruned example, manual manipulation of 16 files per sample is required for discovery. Thus, scientists attempting to leverage single-cell technologies in discovery-focused research beyond a narrow focus face a difficult, non-deterministic, and non-reproducible path. And so, there exists a need in the art to provide data analysis tools that can analyze high-dimension data and find biologically relevant data without the intervention of a highly-skilled expert.

It is in view of the above problems that the present invention was developed. The inventors disclose a framework and interface for invoking and assimilating any external algorithms and interacting with said algorithms in-session and real-time. The inventors also disclose reproducible, updatable nodes and leveraging these nodes for data-driven analysis whereby the data itself can direct the algorithm choice, variables, and presentation leading to iteration and optimization in an analysis workflow. Through these two aspects of example embodiments, an entire discovery or diagnosis process may be executed on a particular data set, thereby divorcing the discovery or diagnosis process from a specific data set such that the same discovery or diagnosis process, phenotype identification, and visualizations may be repeated on future experiments, published, validated, or shared with another investigator.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 2B illustrates an example XML description of a workspace.

FIG. 2C illustrates an example XML description of a plugin.

FIGS. 8B and 8C show an example of expert training of a data discovery node.

DETAILED DESCRIPTION OF EXAMPLE EMBODIMENTS

Figure 1:
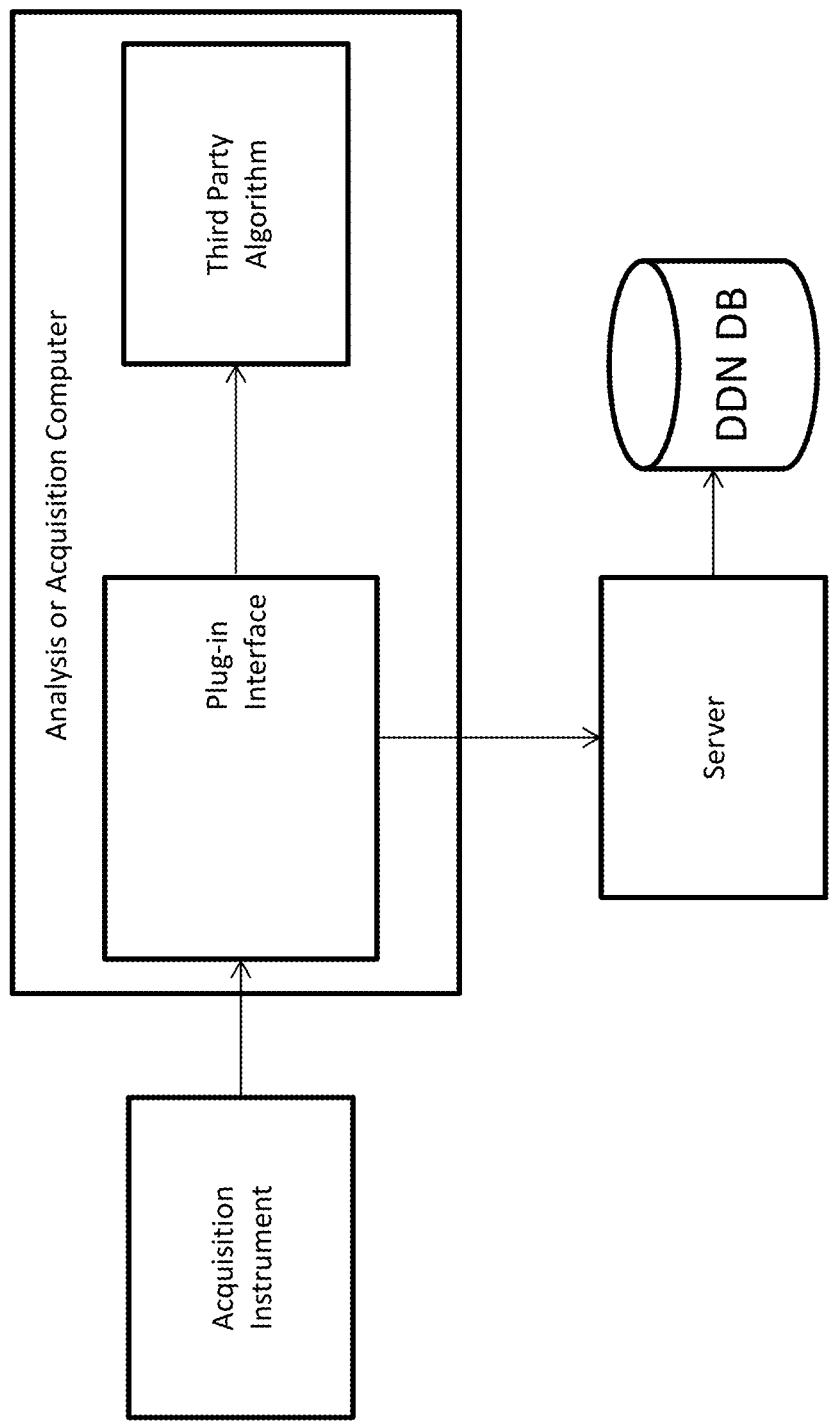
FIG. 1 illustrates a system diagram for an example embodiment.

Referring to the accompanying drawings in which like reference numbers indicate like elements, FIG. 1 illustrates a system diagram. As shown in FIG. 1, a data acquisition instrument is connected to an acquisition computer. In an example embodiment, the acquisition instrument is a flow cytometer. However, it should be understood that instruments other than flow cytometers may be used as the acquisition instrument. However, for the purpose of explanation, flow cytometry will be used as an example embodiment herein as the inventors believe that the technologies described herein are particularly innovative and useful with regard to single cell technologies including flow cytometry.

The analysis computer is connected to a server through a network connection, such as over the Internet, over a subnet, over an intranet, or through the Internet to a cloud. In some embodiments, the acquisition instrument may be connected to an acquisition computer, and the data acquired by the acquisition instrument is analyzed on the analysis computer after transferring the data to the analysis computer The analysis computer executes analysis software, and the analysis software is capable of adjusting one or more parameters (e.g. voltage, flow rate, etc.) of the acquisition instrument for a sample being tested. Such analysis software may also display initial sample information while acquiring sample data to provide feedback for a user to assess whether the parameters are correctly set. The analysis software may vary depending on the manufacturer of the acquisition instrument. In some embodiments, the acquisition computer may execute a light version of the analysis software containing mostly user-interface items, and the server also includes a version of the analysis software. In this embodiment, the server may perform the processing-intensive functions, such as heavy data analysis because the server may have more computing resources than the acquisition computer.

The analysis software may receive data signals from the acquisition instrument indicating results of a sample being analyzed by the acquisition instrument, or the analysis software may receive a data file representing the data collected by the acquisition instrument. In some embodiments (for example, when the acquisition instrument is a flow cytometer), the data generated by the analysis software may indicate any or all of the number of cells in a sample, the number and frequency of peripheral blood mononuclear cells (PBMC), the number of CD4+ T cells, the number of CD14 cells, the number of CD7+ cells, etc. The results of a sample analysis may be contained within one or more flow cytometry standard format files (e.g., a FCS or CSV file). The acquisition computer creates an FCS file based on the signals and data provided by the acquisition instrument. However, it should be understood that other file formats may be used, particularly if the acquisition instrument is not a flow cytometer. The analysis software may further generate metadata about the sample that indicates things such as acquisition instrument ID, patient ID, acquisition conditions and parameters, etc.

The analysis computer also includes an interface that permits the analysis computer to communicate with remote computers, such as an analysis server or a third party server. As an example of the other computer to which the acquired data is transferred, the server may be a remote server dedicated to flow cytometry analysis. In the remote server embodiment, the analysis or acquisition computer may access the server over a network. The analysis or acquisition computer may also communicate with third party computer systems or servers. The analysis or acquisition computer may store and execute third party algorithms, such as algorithms configured to identify populations, to include tracking identification numbers for clinical purposes, or any other external algorithm capable of analyzing data or processing data generated by the acquisition computer. While FIG. 1 illustrates a situation where the analysis or acquisition computer system stores and executes a third party algorithm, it should be understood that a remote computer, such as the server, may also execute the third party, or "external", algorithms. The acquisition computer may communicate with multiple remote computer systems depending on the needs and analysis performed by the acquisition computer.

The server comprises a processor and memory as well as data storage, such as a database. Processor-executable instructions resident on a non-transitory computer-readable storage medium (such as memory) may be executed by the processor to perform tasks described herein. The database may store data discovery node data structures, which are described herein. The acquisition computer may similarly comprise a processor and a memory, and wherein processor-executable instructions resident on a non-transitory computer-readable storage medium (such as memory of the acquisition computer) may be executed by the processor of the acquisition computer to perform tasks described herein for the acquisition computer.

The description that follows will elaborate on a number of different aspects of the inventive technology described herein, including but not limited to (1) a plug-in framework and interface for invoking and assimilating external software algorithms, and (2) a data-driven discovery process making use of data-discovery nodes.

Algorithm Plug-in Framework and Interface

Within the study of single cell assays, scientists and algorithmists continue to generate useful analysis algorithms that streamline analysis of data collected by an acquisition instrument. For example, some external analysis algorithms are configured to identify cell populations.

Conventionally, cell population identification is done manually through a process called gating. Manual gating generally involves a user manually drawing a shape, such as a circle or polygon, around a set (cluster) of data points to identify a cell population. However, advances in life science data analysis have generated automatic gating programs capable of identifying cell populations. Furthermore, the use of a computer processor for cell population identification or any other data analysis step may remove any human-created bottlenecks or biases because the processor-executed algorithms can identify cell populations or conduct other analysis faster and more objectively than manual analysis performed by a human. While population identification algorithms have been given as an example, other types of data analysis algorithms exist that help scientists analyze and interpret data collected by acquisition instruments, such as external algorithms for generating reports or visualizing analysis results and high-throughput genomic and phenomic data analysis such as SPADE, FlowMeans, and algorithms hosted as part of the Bioconductor project.

In addition to external algorithms for population identification, the algorithm plug-in framework and interface may communicate with an external server or remote computer systems to download experiment data from open-source databases, download annotated experiment data from external databases, upload workspace data so that the external server or remote computer system may scan for statistic values, execute application level operations, or to receive tracking identification numbers for clinical trials. The ability to interact with external server systems provides the analysis software with valuable pre- and post-processing of analysis results. For example, if a scientist conducting a clinical trial needs a trial identification number, the algorithm plug-in framework and interface may communicate with the external server to upload clinical trial experimental results for verification purposes.

In yet another embodiment, algorithms that are internal to the analysis software may be compartmentalized in a specific platform, making them inaccessible outside their intended context. Examples of these internal, but inaccessible outside their intended context, algorithms (when the analysis software is FlowJo) may include polynomial fits in a Proliferation platform, +/−peak finding in FlowJo's Compensation Editor, or Gaussian fitting in FlowJo's cell cycle platform. The algorithm plug-in framework and interface described herein not only integrates the external algorithms to the analysis software but also allows for the use of compartmentalized internal algorithms outside of their current, limited context described above.

A plugin system is a mechanism that provides an API to enable external algorithms to run in a product to extend its functionality. External algorithms can typically be used to identify populations by generating a resultant CLR/CSV file (where each row corresponds to an event in the sample), but may also generate additional artifacts, such as reports or tables. In example embodiments, the external algorithm can be implemented in the Java language, or in any other language that can be invoked from Java. To add an external algorithm, the developer will implement a Java interface that is used by the FlowJo product to create a new 'population node' in the workspace, that can then be manipulated like FlowJo's geometrically-gated population nodes to create graphs and statistics.

As shown in FIG. 1, the acquisition computer may store and execute a plurality of software programs and algorithms useful in analysis of data acquired by the acquisition instrument. For example, the analysis software may include a single cell analysis program, such as FlowJo. The third party algorithms may perform processing complementary to the analysis software, such as, but not limited to, automatic population identification programs or external server functions described above. The acquisition computer may execute the external algorithm at the direction of the analysis software. In some embodiments the acquisition computer may execute the external algorithms, and in another embodiment, a remote computer, such as the server shown in FIG. 1, may execute the external algorithm and provide the results of the external algorithm's processing to the acquisition computer over a network.

Figure 2A:
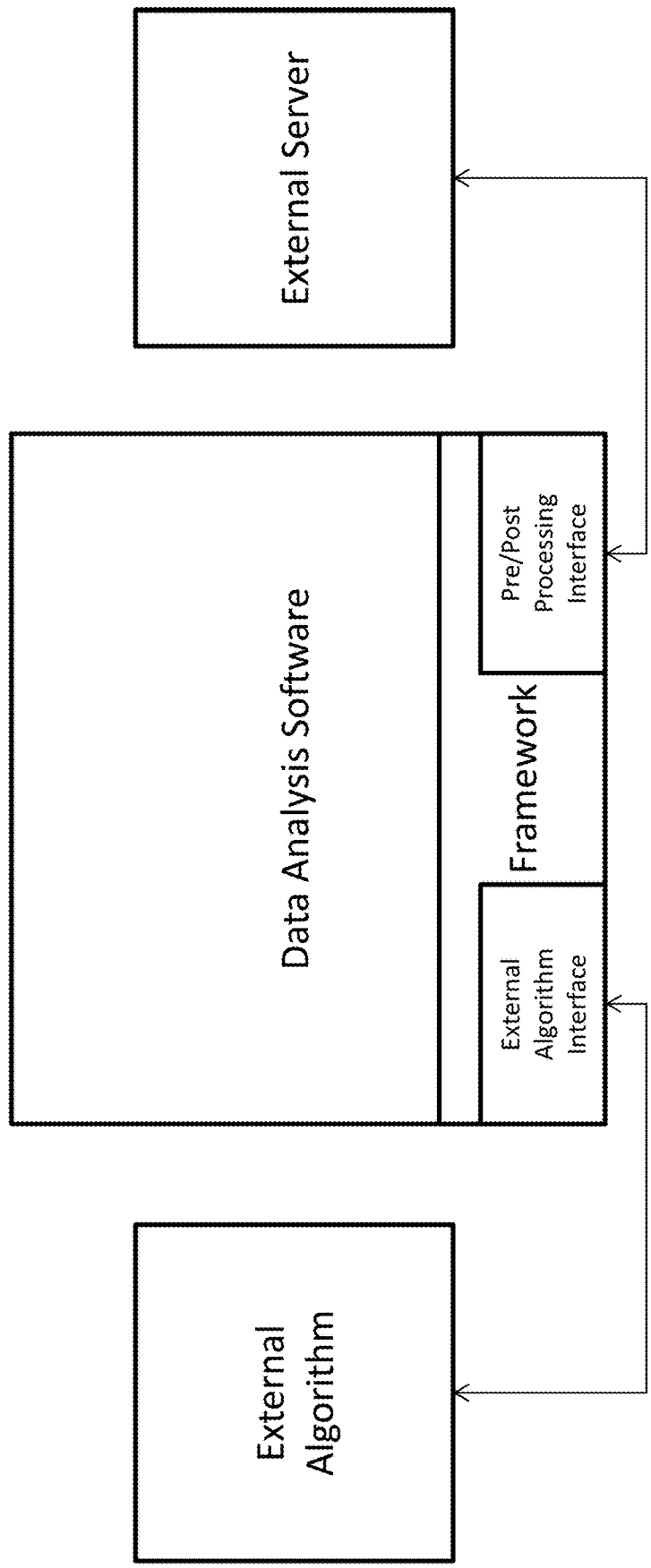
FIG. 2A illustrates a plug-in framework and architecture according to an exemplary embodiment.

FIG. 2 illustrates an exemplary framework and interface for invoking an external algorithm or pre/post-processing of analysis results within a session of the analysis software's processing. The framework described herein may build upon existing scientific data analysis software. For example, if the analysis software is software generated for analyzing flow cytometry data, the framework may call upon an external algorithm to identify cell populations within data gathered by a flow cytometer. The framework for interacting with external servers and external algorithms may be included within the data analysis software.

For example, the framework may include a collaborating set of classes and their sequence of interactions, as defined by a programming language such as Java. While Java is given as an example programming language, one of any number of programming languages may serve as the programming language that executes the processes and framework described herein. While multiple programming languages may achieve the system and method described herein, Java does have certain advantages that make it desirable over other programming languages, namely Java's ability to call out to other programming languages, such as C, R or a web-based calculation engine language. Many external algorithms that perform statistical analysis of data collected by scientific instruments are written in the R language. Thus, Java's ability to call out to R bridges the analysis software to an external algorithm written in R. Of course, if the external algorithm is not written in R, Java may also call out to the external algorithm's programming language.

The framework provides the mechanism by which current and future data analysis algorithms are invoked with an input set of data values, as well as the subsequent processing of analysis results, in the form of event cluster values, formulas, visual graphics, or geometrically-defined boundary definitions. In other words, the framework generates a set of input data and calls upon one of two interfaces to communicate the input data to an external algorithm or an external server. After the external algorithm's processing, the framework receives analysis results from the external algorithm or server and provides a mechanism by which the invocation of the algorithm or pre/post processing is represented and saved in a file. The analysis results saved in the file can be integrated with the analysis software for downstream statistical calculations, graphing of results, or invocation of other algorithms (such as additional external algorithms, subsequent pre/post-processing, or algorithms included within the analysis software).

The framework also manages invocation of integrated algorithms, which are algorithms that are external to the data analysis software itself. The analysis software provides an interface through which biologists can interact with these algorithms. The analysis software, based on the instructions provided by both the biologist (e.g. selecting a particular population on which an analysis is to be run) and the plugin developer (e.g., specifying the requirements for the data which the algorithm needs as input (e.g. a CSV file corresponding to the data values of the population which the biologist has selected) and, following an analysis, where and what type of output will be available for the plugin interface to present to the user). The interface also serves as the agent through which updates in analysis are communicated, such that analysis always stays hierarchically correct and biologically relevant. More specifically, not only does the framework invoke integrated algorithms when an analysis is first run, but the framework also re-executes an integrated algorithm whenever the input set of data values change. Therefore, scientists can run analysis quickly on multiple sets of data inputs, and the framework will invoke and re-execute the integrated algorithms without user interaction anytime the input data values change or the user changes experiment parameters. For example, changing some data parameters may change how populations are identified by an integrated algorithm. Upon noticing a change in data input, the framework invokes the integrated algorithm to re-identify the populations, and the framework uses the analysis results generated by the integrated algorithm. Upon receiving the analysis results from the integrated algorithm, the framework may provide the results to the analysis software in a data format understood by the analysis software, and the analysis software may perform downstream analysis on the results, such as statistical analysis, graphing, or reporting.

The framework allows algorithm integration to be saved as a workspace so that workspaces may be saved and re-opened for further analysis.

The framework includes an interface for communicating with remote computer systems and an interface for communicating with external algorithms. Each interface provides a means by which external algorithms or functions stored on external servers may be invoked without user interaction. In fact, to the user viewing the data processing through a graphical user interface, the invocation of an external algorithm is invisible, as only the results of the analysis performed by the external algorithm may be shown to the user, such as through statistics, graphs, or other reports generated by the analysis software.

Generally, the interfaces for invocation of the integrated algorithms include, but are not limited to, an input file of data values, an output folder destination, and an XML description of a data set from one or multiple experiments. This XML description may include pointers to raw data, all analysis executed including plugin-driven analyses, meta-information about the data, and data transformations that are optimally used to process and visualize the data such as logicle, biexponential, hyperlog, and hyperbolic arcsin. The XML description may take the form of an XML document that specifies this information via markups hierarchically links raw data to the analysis and associated results. FIG. 2B shows an example XML description of a workspace, and FIG. 2C shows an example XML description of a plugin. It should be understood that forms other than XML may be used, such as proprietary binary files which can store the same data and analysis architecture. Furthermore, the description of the data set, whether in XML or another format, can include the metadata regarding input parameters for any plugin-based analyses and pointers to any derivative data produced by the external algorithms. Whether the XML meta-information is used by the external algorithm depends on the algorithm invoked. The external algorithm interface also defines steps for the algorithm invocation to be saved and later restored by the framework. The interface is able to receive analysis results from the integrated algorithm in the form of graphics, derived parameters, tabular data, gating data (such as in the Gating ML format), classification results files (CLR), XML data, or comma separated values (CSV) files. Said differently, the interface is configured to manage artifacts generated by integrated algorithms.

The interfaces define a contract by which the external algorithms and server functions must adhere to plug the external algorithm into the analysis software. The external algorithm interface and the pre/post processing interface each define a contract for interfacing with pre/post processing on an external server or interfacing with an external algorithm. The different interface implementation steps are illustrated in more detail in FIGS. 3 and 4.

Figure 3:
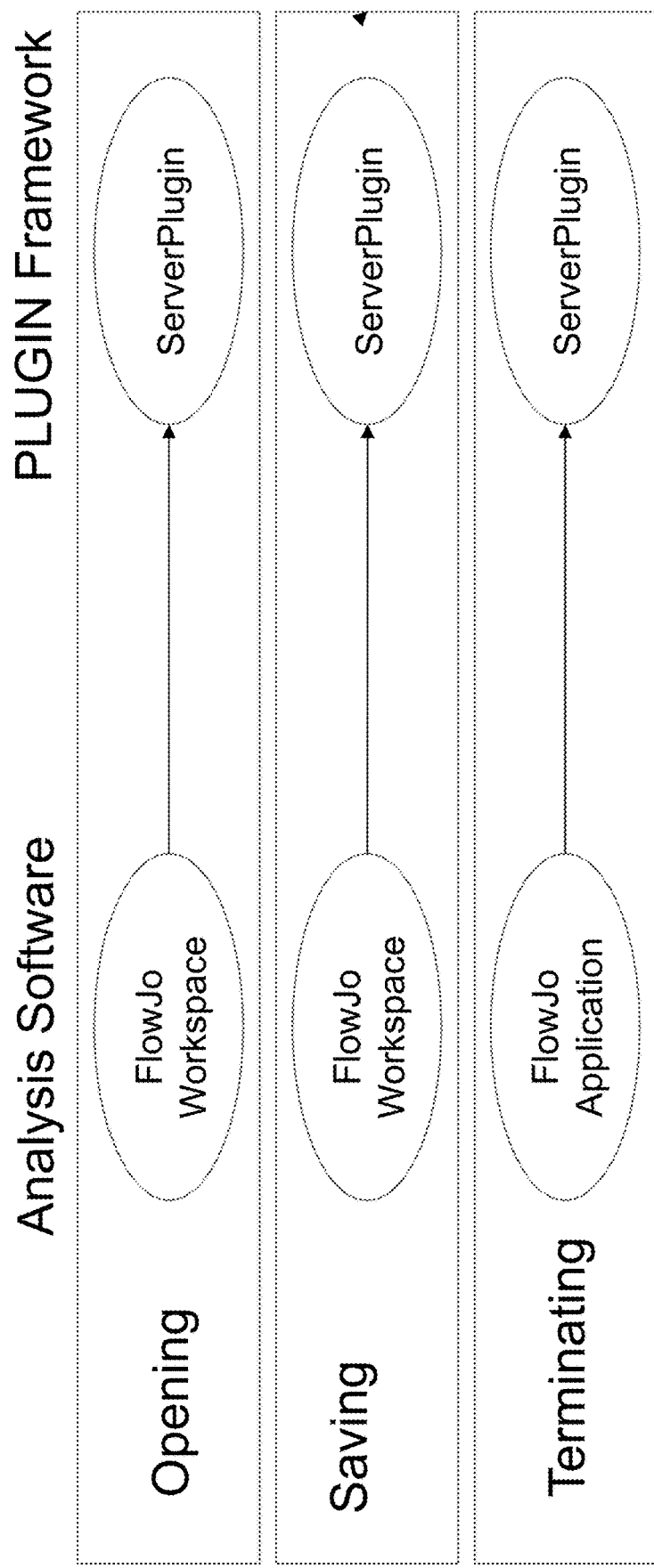
FIG. 3 illustrates an implementation for interfacing with a remote computer using the plug-in framework and architecture.

Referring to FIG. 3, the implementation steps for interfacing with a remote computer are illustrated. The method begins with the interface opening a workspace. Opening a workspace includes a processor reading the XML of a workspace and the XML of the pre/post-processing interface. While the workspace XML contains the metadata associated with each sample (date acquired, instrument type, parameter names, etc.) as well as any user-defined, sample-specific metadata added post-acquisition, the XML specific to the plug-in interface retains variables necessary for the execution/updating of a plugin module e.g. URI of a database or server. As a result of reading the workspace and receiving the URI, the processor establishes a connection to a server or data store (e.g. database) stored therein to initiate authentication as described below, execute a query, and retrieve data from a database and modification of the workspace XML. The workspace opening step further comprises the pre/post-processing interface, executed by the processor, augmenting or modifying the XML workspace (input to the analysis software) based on retrieval from a database (e.g. a Laboratory Information Management System (LIMS) for sample tracking which includes metadata and analysis instructions for a specified data files). Additionally, the XML input may be modified to add gates, statistics, sample names, or anything that may be contained in a workspace XML. As long as input adheres to a defined schema defined by the analysis software, these additions may invoke calculation and representations in the analysis software. Validation and well error reporting of the input is handled through the interface, and validation suites for testing input are run at deployment. It may also perform authorization, which may come in the form of making sure the analysis software has access to the server, determining whether the external server is online, exchanging credentials, or any other authorization step. XML augmentation may comprise the processor generating or changing the metadata to reflect that the pre/post-processing step is to be performed by the remote server.

Next the method saves a workspace within the analysis software. The saving step comprises the processor saving the workspace and the pre/post processing interface's state. The plugin will update its own XML representation in the workspace to retain its 'state' and/or may traverse the XML to extract data and perform an action e.g. updating a database with specified statistics. During this step, the pre/post-processing interface may generate additional artifacts such as SQL output or a log of analysis actions taken, and the pre/post-processing interface communicates with an external system. During this communication, the interface provides input data to the external system and receives data from the external system, such as downloading data collected and annotated according to the MIFlowCyt standard, receiving a tracking identification number from a clinical tracker, or any other pre/post processing step. The pre/post processing interface may reference a server URL to make this communication.

After completing the communication with the external server, the processor terminates the session, and the pre/post processing interface frees up computer resources, such as database connections.

Figure 4:
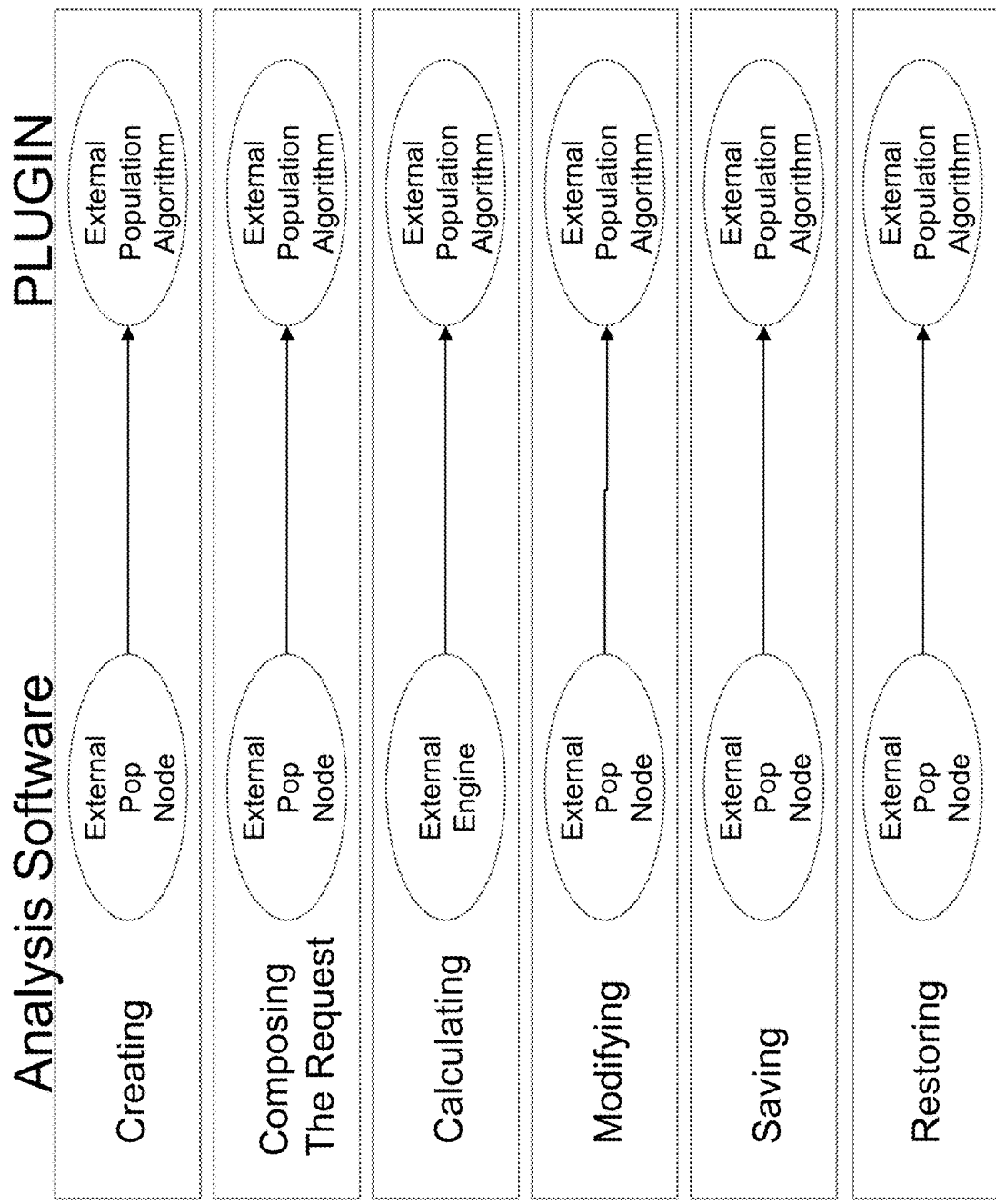
FIG. 4 illustrates an implementation for interfacing with an external algorithm using the plug-in framework and architecture.

Referring now to FIG. 4, the implementation steps for interfacing with an external algorithm are illustrated. The method begins by creating an external population node, which may be defined as a wrapper for the external algorithm interface. During this creation step, the processor may prompt a user with options relevant to the external algorithm, such as setting parameters, setting operation variables, naming files, etc., but this user prompt step is optional and may depend on the external algorithm invoked.

Next, the processor composes an engine request by generating an XML representation to invoke the calculation performed by the external algorithm. The XML representation represents what algorithm to execute or visualization to generate, and the associated inputs and arguments necessary e.g. file path, number of parameters, number of clusters, variables for dimension reduction, color selection, type of visualization, image type for saving, etc.

After composing the request, the processor invokes the external algorithm. Invoking the external algorithm includes providing the external algorithm with an FCS file, XML included with the FCS file (including number of events, sample file name, and population name), and an output folder where the external algorithm should save its results. In response, the external algorithm performs its processing and calculations. After the external algorithm performs the requested processing and calculation, the analysis software interface receives the results and integrates them into the analysis software. These results may come in the form of a CSV file, a CLR file, a GatingML file, or an FCS file. When importing a CSV or CLR file, each row of the CSV or CLR file corresponds to an event in an FCS file and column number correspond to the cluster number. Furthermore, the external algorithm interface creates a derived parameter, and the analysis software automatically gates on the derived parameter to create sub-populations. After receiving the results, the processor may modify the inputs to the algorithm. In one embodiment, the processor receives the external algorithm's results by referencing the data stored in the given output file.

After receiving the results from the external algorithm, the processor saves the workspace in a file system and restores the analysis software workspace. The processor may then perform additional downstream analysis at the direction of the analysis software.

In this way, external algorithms and functions stored on external servers are available to the analysis software without a full integration into the analysis software. A user of the analysis software gains innumerable more analysis options and functionality without major workflow hacking or command line knowledge. Instead, the user may use the graphical user interface of the analysis software to invoke external algorithms or external functions stored on servers seamlessly.

Data Discovery Node Architecture and Process

Within the analysis software, a "node" represents an entire analysis step, such as a step of defining a geometric cluster using geometry-based tools or applying statistical analysis to data acquired by the acquisition instrument. Such "nodes" represent a processing step or calculation with an input, a full set or a subset or event-level raw data, and an output, such as a geometric definition of a cellular subset, or a mathematical model (e.g. percentage of cells in the cell cycle). In other words, a node is a data structure created by the analysis software instructing the analysis software to perform an analysis calculation, such as population identification, statistical calculation, a mathematical function, geometric gating, presenting results, augmenting results or the like. In addition, the node data structure includes a specification of the data to input to the analysis function and the way to present the results, such as in a CSV file, a GatingML file, etc. The data structure may furthermore be conditional on the type of data input.

The technology described herein extends the node concept described above so that a user can specify and perform data analysis on a data sets through a "data discovery node" (DDN) framework within a data analysis application, where the DDN framework provides the data analysis with access to a wide knowledge base beyond the whatever intelligence may already be resident in the data analysis software itself. For example, a DDN can also encapsulate decisions that can be made from external algorithms plugged into the analysis software using the plug-in interface and framework disclosed above. Algorithm-based decisions remove subjectivity of analysis by shifting the decision-making away from an individual analyst, who has subjective bias, to a data-driven algorithm. The data discovery node architecture and process described herein also transforms a unidirectional node into an active node that accomplishes at least the following four goals: 1) an active node allows for repeated, reproducible analyses to provide comparison between samples, groups, and studies (i.e. not affected by subjective bias of an analyst); 2) an active node lowers the barrier to complex analyses and reporting through drag-and-drop mechanisms; 3) an active node remains live for updating should the input data change; and 4) an active node facilitates automation as nodes can be stacked in an analysis and run in command line mode.

Figure 5A:
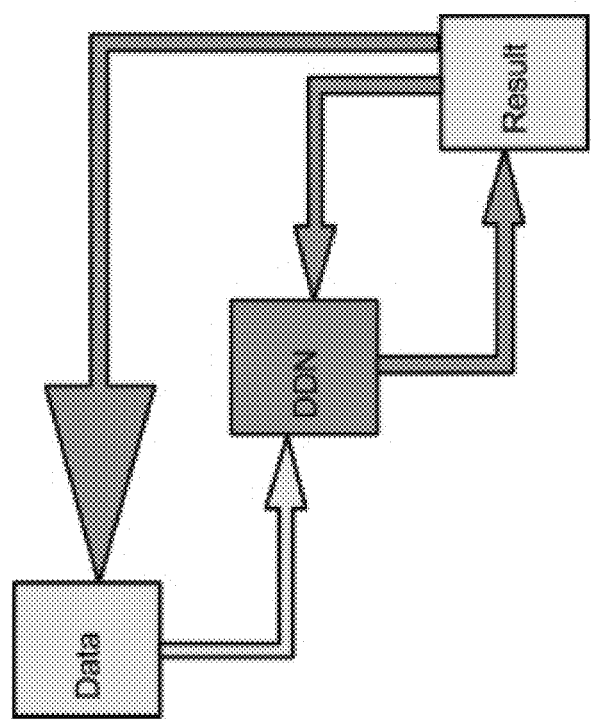
FIG. 5A illustrates a high level representation of a data discovery node process with result feedback according to an exemplary embodiment.
Figure 5B:
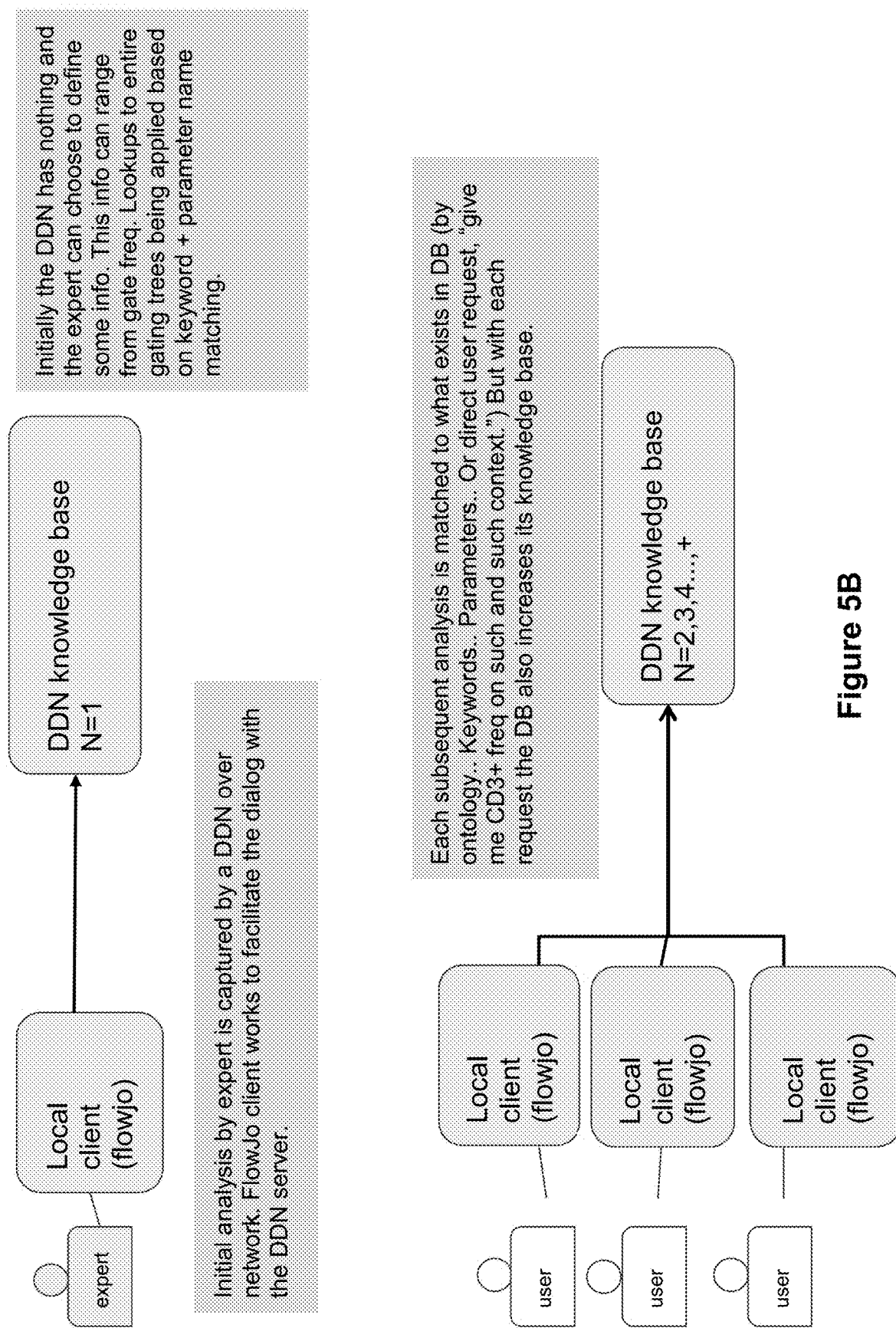
FIG. 5B illustrates an example of how data discovery nodes can be used to expand a knowledge base.

FIG. 5A represents the active node architecture. The DDN framework according to an example embodiment includes the following components: software, data structure, algorithms, and a database accessible over a network. As noted above, the DDN framework in the data analysis application is fundamentally a way for a user to access a knowledge base which is built upon each application of the node. Thus, the user gestures via a user interface to create a DDN for the analysis to be completed, and indicates what type of analysis is to be completed. The end-user instance of the DDN (which is physically manifested as a "node" in the workspace) does not contain the knowledge but rather it allows the user to plug into the greater context of what they're analyzing (ex. reference CD3+ percentage in Elderly Humans.) For example, a. user creates a CD3+ gate to identify a T cell population as a gate node,
b. the node is assigned as a DDN by the user in the user interface (at the local client, i.e. "make this a DDN") which has two consequences:
   i. The following population and sample information is written to the physical memory of the knowledge base:
      1. "sample information"
         a. metadata contained in the FCS (raw) file e.g. on which instrument, by what acquisition software
         b. sample context (cell type, species) will send to the DDN knowledge
      2. DDN execution parameters, outlined below.
      3. Biological result information—the statistics and numerical results of an analysis
   ii. if the DDN is in iteration n>1, the DDN returns to the user any flags, such as "based on my data, this CD3+ frequency is two standard deviations below previous observations."
c. Thus, the knowledge base provides a reference, and the DDN provides a two-way dialog between the analyst at hand, and all the previous analysts' data that matches the current pattern as established via the aforementioned example DDN parameters (see FIG. 5B). The DDN is the user-facing node which enables the component that "drives" this exchange i.e. the hosted network (separate from the processor that accesses the "raw" data file.)

As shown by FIGS. 5A and B, input data is provided to the DDN, and the DDN performs an analysis step that produces a result. The resulting data generated by the DDN may be fed back into the DDN, or the resulting data changes the input data, such as by pruning the input data, removing noise from the input data, or changing a parameter of the input data. When the resulting data affects the input data in anyway, the DDN may apply the same analysis step with the new data set, or the DDN may apply a different analysis step based on the new data set—in this way, the DDN may be considered "data-driven" after the first iteration.

Furthermore, the resulting data may have further bearing on downstream processing. For example, the DDN may represent a population identification algorithm, and the resulting data may produce inconclusive or undesirable results. The node can analyze the resulting data, and based on the analysis of the resulting data, the DDN can change parameters of the population identification algorithm to better identify populations within the input data. In another example, the resulting data may determine that an identified phenotype (e.g. CD8+) has no correlation with morbidity or therapeutic efficacy. If no correlation to morbidity or therapeutic efficacy can be found by the resulting data, the DDN or a scientist training the DDN may instruct the DDN to ignore this phenotype for future analysis. In this way, the DDN optimizes to most accurately identify populations using a referenced population identification algorithm. As can be seen by the example above, the data and the algorithm drive decisions made by the DDN. The more data the DDN receives, and the more the DDN processes, the more the DDN learns. This data-driven method will be described in more detail below.

It should also be noted that a practitioner may choose to include a security or curation layer in the DDN framework so that the framework is less susceptible to attacks. This could help prevent bad or untrained actors from fouling the knowledge base (for example, 100 people gating an erroneous CD3+ frequency of 1% and submitting that bad data).

Figure 6:
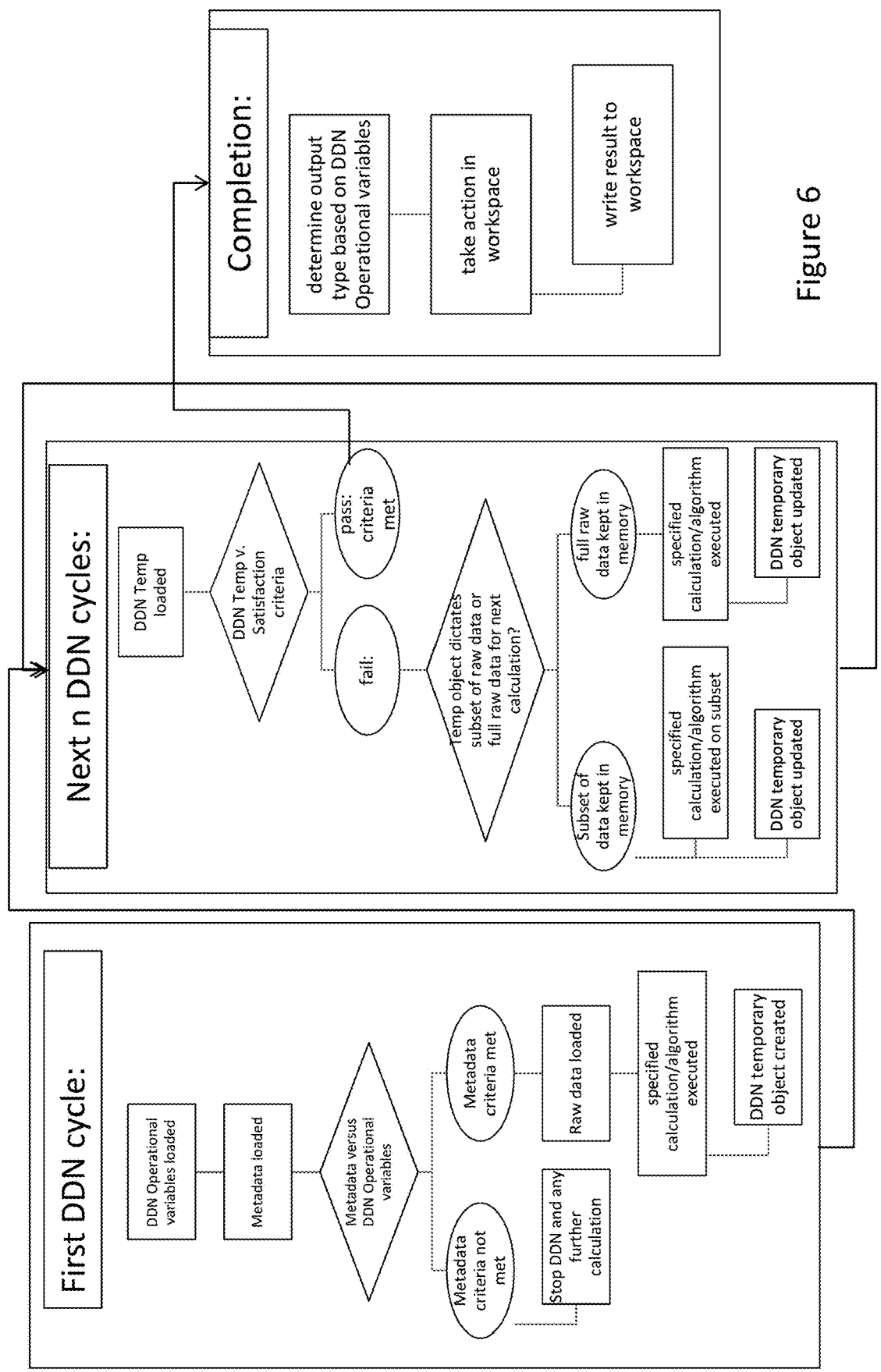
FIG. 6 illustrates an entire life-cycle for a data analysis flow performed by a data discovery node.

FIG. 6 illustrates a life-cycle for a data analysis flow performed by a DDN. In the process illustrated by FIG. 6, method steps illustrated as a rectangle represent an action step performed by the processor, method steps illustrated as a diamond represent a test step or a determination step performed by the processor, and the method steps represented by an oval represent the possible results of a test step.

At a high level, the method represented in FIG. 6 includes three phases: a first DDN cycle, a next n DDN cycles phase, and a completion phase. The first DDN cycle phase is only performed once, whereas the next n DDN cycles may continue to iterate until a satisfaction criteria is met. The method will enter the completion phase only after the satisfaction criteria is met.

The types of data objects that define and control DDN function will now be described to better understand how the method depicted in FIG. 6 operates. These data objects include operational variables, temporary objects, pointers, metadata, and raw listmode data.

First a DDN includes operational variable data objects. Operational variables are variables set by either a user or the analysis software which contain 1) satisfaction variable thresholds, 2) metadata rules, and 3) a specification of the analysis software algorithm or operation to perform on specified data The satisfaction variable may be a threshold set by the use which must be satisfied to consider the DDN cycle complete. The metadata rules define criteria that must be satisfied by the input. For example, a metadata rule may specify that the input data exhibit a CD4 parameter in the raw data's metadata. The analysis software algorithm or operation specified may include an external algorithm, a mathematical function included within the analysis software, or any other function contained within the analysis software, such as FlowJo's polyvariate graphing, FlowJo's report generation, generating a geometric mean, population identification, or any other function offered by the analysis software or a plugged-in external algorithm.

Figure 7:
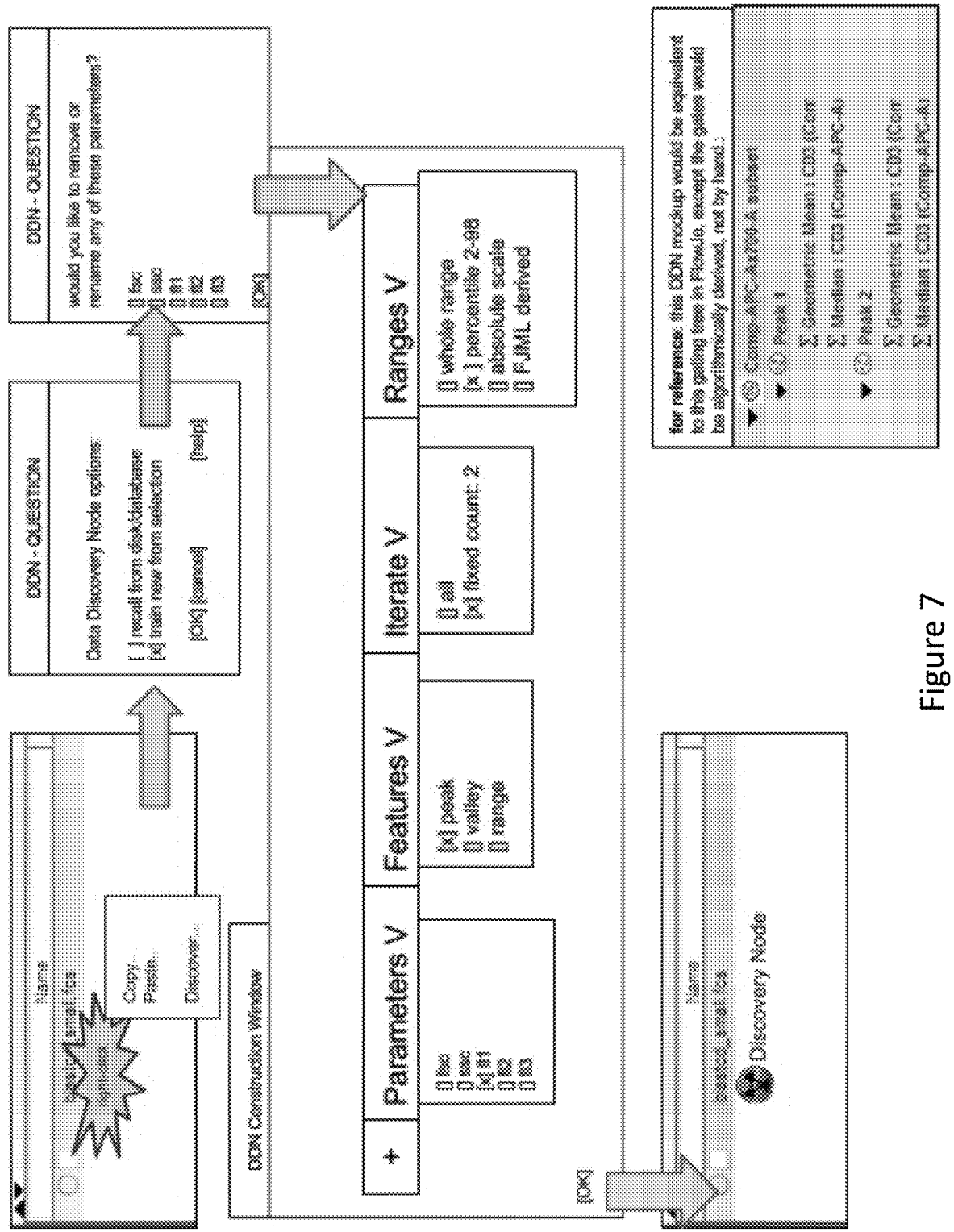
FIG. 7 illustrates a user interface used to create a data discovery node and set and define operational variables.

FIG. 7 illustrates a user interface used to create a DDN and set and define operational variables. First, a user selects a file and gestures to discover. The file may be a set of data collected from the acquisition instrument and saved to a disk drive within the acquisition computer. This gesture informs the analysis software that the user wants to apply a DDN to the selected file. The gesture may comprise a user right-clicking a file, using a keyboard shortcut, clicking an icon within a graphical user interface, or any other gesture understood by the processor. After gesturing to discover, the user can either select to train a new DDN or apply a DDN saved in a database or other file storage container. If the user selects to recall a DDN from a database, the acquisition computer calls out to the database storing DDN data structures, presents a list of saved DDNs, and allows the user to select one of the DDNs for analysis (not illustrated). If the user selects to train a new DDN, the acquisition computer presents, through a graphical user interface, a list of operational variables that will define the DDN.

FIG. 7 illustrates a set of exemplary operational variables for selection, but the present disclosure is not limited to the operational variables shown in FIG. 7. The operational variables may be grouped into sets, such as parameters, features, iteration variables, and range variables, but more groups of operational variables may be defined and presented within the user interface. For example, the user may select from parameters such as, but not limited to, forward-scattered light (FSC), side-scattered light (SSC), fluorescent 1 (fl1), fluorescent 2 (fl2), fluorescent 3 (fl3), fluorescent n, etc. Parameter selection is plays an important role in single cell analysis, and the DDN contains metadata about its own operation in addition to the types of data to which it is applied, i.e. "execution parameters". Examples of selected parameters may include:
  a. The parameters on which the cell phenotype was defined. Using flow cytometry as an example, scatter parameters are relative measures of size and granularity, useful in identifying major cell subsets, e.g. in blood, whereas fluorescent parameters are measurements of biological molecules. Thus parameters are fundamentally not interchangeable, and the parameters used at the selected level for a DDN and its hierarchy are biologically relevant information which facilitate the reproducibility of analysis.
  b. The parameters regarding the type and input variables for any algorithms used to identify a population, e.g. gating and analysis information (vertices, location of adjacent populations, gate type, population characteristics (convex, rare, etc.) population name, parameters on which the gate was drawn, parent gates (ontology), algorithm used to identify population).
  c. The number of types of hierarchical analysis (and thus order of operations) for a series of algorithms and calculations.

In this way, a researcher may specify a population of CD8+ T cells, which were identified by a k-means clustering algorithm (where k=3 was the input variable) executed on CD4 v. CD8 fluorescent parameters, which are children of the CD3+, live, and lymphocyte geometrically defined gates. The DDN allows transmission of this information to and from the knowledge base.

The user interface gives a user the ability to rename these parameters as well. A user may also exclude any of these cytometer preset parameters to limit the amount of data to be processed by the DDN. The DDN receives a selection of parameters to analyze, features to analyze (such as a peak, a valley, or a range), whether to iterate, and which ranges to analyze. After selecting these and potentially other operational variables, the computer creates a new DDN, which will also be saved in the DDN database. The created DDN is ready to analyze the data, generate results, or any other function contained within the analysis software or accessible to the analysis software through the plug-in interface and framework.

To set up a DDN, the processor receives a selection of input data, which is a set of events or a set of files with some implicit sense of equivalency (e.g. CD3 measurement captured across multiple time points). The input data may be a single sample or a group of samples. After selecting input data, the processor may determine the types of analysis available depending on the input data. Once a DDN database is setup, the first step is to have "experts" seed the knowledge base with both sample information and execution parameters to create a reference set. Continuing our example above, the CD3+ data from Elderly Patients is defined by an expert. The non-expert creates a DDN on a 'new' sample, and the DDN compares both sample and execution parameters to examine if it can re-create the expert-driven analysis. Once that match exists, it compares the biological result information—the current measurement v. the knowledge base. The "training" of the DDN via building information in the knowledge base accrues with usage, so each query into the CD3+ part of the knowledge base deposits new biological result information into the pool of known ranges. This two-phase approach validates (1) that an analysis can be applied and executed and (2) compared to a knowledge base of reference data.

In other words, what the DDN can calculate and execute depends on the input data. In one example, the processor may determine whether CD4 events are present in the loaded metadata to determine whether the process may execute CD4 population identification algorithms on the selected data.

FIG. 7 illustrates the exemplary user selections of fluorescent 1 as a parameter, a peak feature, a fixed count iteration variable of 2, and a percentile from 2-98 for the range variable. After the user sets the operational variables, the user interface displays the created data discovery node underneath the selected file. The user may rename the data discovery node for future reference, but for illustration purposes, FIG. 7 merely illustrates the created data discovery node as named "Discovery Node". These exemplary selections for the data discovery nodes are equivalent to a gating tree, which is also illustrated in the bottom-right corner of FIG. 7. Thus, the selection of the exemplary operational variables shown in FIG. 7 equates to the gating tree:
  Comp-APC-Ax700-A subset. This is a subset that would usually be manually defined. In this example, the DDN, via its parameters outlined above, identifies this population algorithmically using the information from the knowledge base, performs peak finding (another algorithmic method for population identification) and then invokes the calculation of statistics to the child subpopulations, in that order.
  Peak 1
    Geometric Mean: CD3(Comp-APC-Ax700-A subset). The user has calculated the geometric mean of the Comp-APC-Ax700-A subset population using analysis application tools, The diagram at bottom right of FIG. 7 shows the hierarchy of this analysis and representation to the user.
    Median: CD3 (Comp-APC-Ax700-A subset)—As above for the geometric mean, but in this case for the median.
  Peak 2
    Geometric Mean: CD3(Comp-APC-Ax700-A subset)
    Median: CD3 (Comp-APC-Ax700-A subset)

Referring again to FIG. 6, in addition to operational variables, the DDN generates a temporary data object after the first calculation. The temporary data object represents a DDN progress object. The temporary data object may at least contain iterations of calculation and satisfaction variables. The iteration of calculation increments for each additional calculation that is performed by the DDN, and the satisfaction variable indicates the status of the satisfaction variables during a cycle of the Next N DDN Cycles Phase. For example, the satisfaction variable may indicate whether the satisfaction variable threshold has been met or exceeded. These data objects allow the DDN to retain statefulness through comparison of the satisfaction variable threshold to a DDN-created temporary data object created at each iteration.

The pointers, which are unique identifiers, point to one or more nodes within the workspace to which the DDN will access for its sequence, which will be further described below. The pointers point to the location of files that contain the metadata and raw listmode data, which are also important to the operation of a DDN.

The metadata important for the DDN comes from the references notes of two different types. First the metadata may come from the decisions made by an expert, which are generally in the form of gates defined by the expert, to get a particular subset of the data. The subset of data may come from hierarchical gates. In a specific example, the XML hierarchy of preceding gates provides contextual information represented in the metadata for use by the DDN data structure. Alternatively to expert decisions, the metadata may comprise keyword metadata from the parent FCS files including a parameter for a stain name ("CD3-FITC"), which is biologically meaningful. The metadata is associated with the raw data, and the metadata associated with the raw data may also include headers of FCS files that are the source of the raw data to be analyzed and a node name.

Finally, the raw listmode data comprises the raw event/cell level data for n parameters collected per event/cell.

The method illustrated in FIG. 6 uses all the data objects described above. The DDN method/life cycle begins with the First DDN Cycle Phase. In the First DDN Cycle Phase, the processor loads the operational variables into memory. Subsequently, the processor loads the metadata described above. The processor loads the metadata and operational variables, which define the rules and variables for testing, before the processor loads the files to be analyzed through the DDN flow.

After loading the operational variables and metadata, the processor tests metadata against the metadata rule operational variable(s) to determine if the metadata meets the criteria of the DDN. For example, if the metadata rule operational variable specifies a metadata parameter to indicate that CD4 cells are present, either through keyword metadata set by a user, phenotype metadata set by an FCS file, stain identification metadata, or any other metadata included within a file generated by an acquisition instrument.

Testing the metadata against the operational values may have a plurality of modes, such as a loose mode, a moderate mode, and a strict mode.

The loose mode may have no metadata requirements. In the loose mode, the DDN will execute regardless of the values of the metadata. For example, in the loose mode the DDN calculates a local minima between two points in the listmode raw data provided, then the DDN will cause the loading of the raw data into memory, invoke the calculation, and complete by adding a statistic to the workspace to be represented to the user.

In the moderate mode, a threshold of metadata matching is set by the user, for example if 3 of 6 parameters for the DDN are set, then the DDN executes as it has sufficient parameters on which to identify cell populations in the data space.

And in the strict mode, all metadata requirements must be met for execution of the DDN to initiate and the processor does not load the raw data into memory, the DDN method stops, and no further calculation is performed.

The metadata will either meet the criteria of the metadata rule operational values or it will not meet the criteria set by the operational values. If the metadata does not meet the criteria of the operational values, the processor does not load the raw data into memory, the DDN method stops, and no further calculation is performed. If the metadata meets the criteria of the operational values, the processor loads the raw data into memory. Raw data loaded into memory may come in the form of raw acquisition data, data from another node, data from one or more gates, or any other raw data accessible to the analysis software.

After loading the raw data, the processor executes the calculation or algorithm specified by the operational variables. For example, the processor may execute an external algorithm using the plug-in architecture and framework described herein to identify one or more populations within the raw data. In addition, the processor creates the DDN temporary object described above. Creating the DDN temporary object involves the processor setting the iteration variable to a beginning number and defining the satisfaction value based on the result of the executed calculation or algorithm. After creating the DDN temporary object, the First DDN Cycle Phase completes, and the processor begins execution of the Next n DDN Cycles Phase.

In the Next n DDN Cycles Phase, the phase begins by loading the DDN temporary object and determining whether the DDN temporary object's satisfaction value meets or exceeds the satisfaction threshold or satisfaction criteria set by the operational variables. Comparing the DDN temporary object to the satisfaction threshold may comprise the processor comparing the iteration variable to the DDN's satisfaction variable. For example, if the satisfaction variable instructs the DDN to iterate 5 times, and the temporary object's iteration variable is less than 5, the satisfaction variable will not be met and the DDN will iterate again. As another example, the processor may determine if the DDN temporary object or any other operational variable has specified a "direction" for the next calculation. For example, a direction specified by the DDN temporary object may indicate that only a subset of the raw data in memory should be used in the next iteration. As another example, the satisfaction value may comprise a value indicating accuracy—such as by defining a percentage of events in a category, and the processor may compare the accuracy number to the satisfaction criteria. An example of an accuracy number may include analysis of a three-color flow of estimating purity and recovery of a scatter gate. Here the scatter gates could be redefined until the best combination of purity and recovery were reached. The optimization loop would shrink and grow a gate applied to all samples until the purity effect and recovery effect values were over 90%.

If the DDN temporary object's satisfaction variable meets or exceeds the satisfaction threshold or satisfaction criteria, the processor executes the completion phase.

If the DDN temporary object's satisfaction variable does not meet or exceed the satisfaction threshold or satisfaction criteria, the processor determines whether the temporary object dictates a subset of the raw data loaded into memory or the full set of raw data loaded into memory for the next iteration. Recall from above, that the operational variables may indicate whether to execute a calculation or algorithm on a subset of data or the full set of data. For example, the operational variables may indicate that a set of data should be gated using an external algorithm, and the downstream mathematical calculations are to be performed only on the gated data. It should be noted that the metadata may instruct the processor to analyze the data or raw listmode data's metadata to determine which calculation or algorithm to apply. The metadata may call for branching or decisions trees to be executed by the processor before executing a specified calculation or algorithm. For example, if the processor analyzes the raw data such that it suggests CD4 events, the processor may apply a CD4 population identification algorithm, whereas if the processor analyzes the raw data such that it suggests CD8 events, the processor may apply a CD8 population identification algorithm.

If the operational variables specify the full set of data, the processor executes a specified calculation or algorithm on the full set of raw data, and the processor updates the temporary object by incrementing the iteration variable and redefining the satisfaction value based on the result of the executed calculation or algorithm on the full set of data. The full set of data may remain in the memory during these phases. After updating the temporary object, the processor repeats the Next n DDN Cycle based on the new temporary object values.

If the operational variables specify a subset of data, the processor executes a specified calculation or algorithm on the specified subset of raw data, and the processor updates the temporary object by incrementing the iteration variable and redefining the satisfaction value based on the result of the executed calculation or algorithm on the subset of data. The data not included within the specified subset of data may be released from memory and stored elsewhere. After updating the temporary object, the processor repeats the Next n DDN Cycle based on the new temporary object values.

The Next n DDN Cycle Phase continues until the satisfaction threshold or criteria is met or exceeded. Once met or exceeded, the processor continues to the Completion Phase where the processor determines an output type, which is specified by the operational variables. In the iteration options, the user may set the number of iterations which are stored as the DDN execution parameters. Based on this determination, the processor takes action in the workspace and writes the result of the DDN flow to the workspace file. For example, the processor may present one of a plurality of visualizations depending on the result and the action taken, or the processor may define a new population or statistic within the workspace file.

The action taken in the workspace, which occurs in the Completion Phase, may involve re-invoking the DDN with new input data. For example, the output generated during the Completion Phase may be a new input data set. When the input data set changes, the DDN may again invoke and perform the processing. Thus, whenever an input data set changes, the DDN may perform its necessary processing.

Figure 8A:
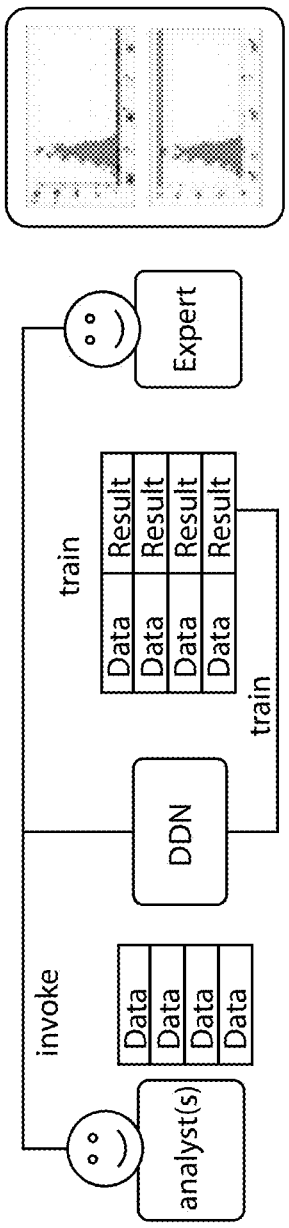
FIG. 8A illustrates an expert training a data discovery node and an analyst invoking the expertly trained data discovery node.

Referring now to FIG. 8, in any experiment, clinical trial, study, research project or the like, the number of experts is limited. That is, the more someone knows about an area of study, topic, cell phenotype, scientific property, etc., the fewer of those experts exist, and the experts' time is limited. However, analysts, who may be highly skilled and knowledgeable, but lacking the wealth of knowledge possessed by an expert, are much more common and plentiful. Due to the shortage of experts and abundance of analysts, an expert generally delegates some tasks, such as running experiments, to analysts, while the expert oversees the analysts work product. However, conventional methods did not allow an expert to see each individual step of an experiment and analysis, such as how geometric gates were applied because an expert simply lacks the time to review all analysis steps from every experiment analysis he reviews.

In contrast to conventional methods of expert utilization, FIG. 8 illustrates the process of training a DDN by an expert so that analysts may invoke and deploy an expertly trained analysis flow to an acquired set of data. As mentioned above, an expert may provide training to a DDN data structure by setting the operational data structures of the DDN and by using the knowledge gained by the DDN through the saved temporary object, and the expert's decisions, such as in the form of hierarchical gating, may be saved and represented in the DDN's metadata. FIG. 8 illustrates the expert training a data discovery node using his own expertise and experience. The training process may comprise some or all of the steps illustrated in FIG. 6. The expertly trained DDN may represent a portion of an analysis flow or an entire analysis flow. For example, the expertly trained DDN may apply a geometric gating technique that is precise based on the expert's knowledge. Alternatively, the DDN may include analysis steps that call out to an external discovery algorithm for population identification, and the expertly trained DDN may provide specific parameters for the discovery process provided by the expert. Because the expert trained the DDN, specified the flow steps, specified limitations on population identification, and specified any mathematical models, the DDN removes any bias that the analyst may bring to the analysis. With the DDN framework and processes discussed herein, analyst bias is removed, and all experiments performed using a DDN will be performed in the same way, which gives rise to uniform results.

Figure 8B:
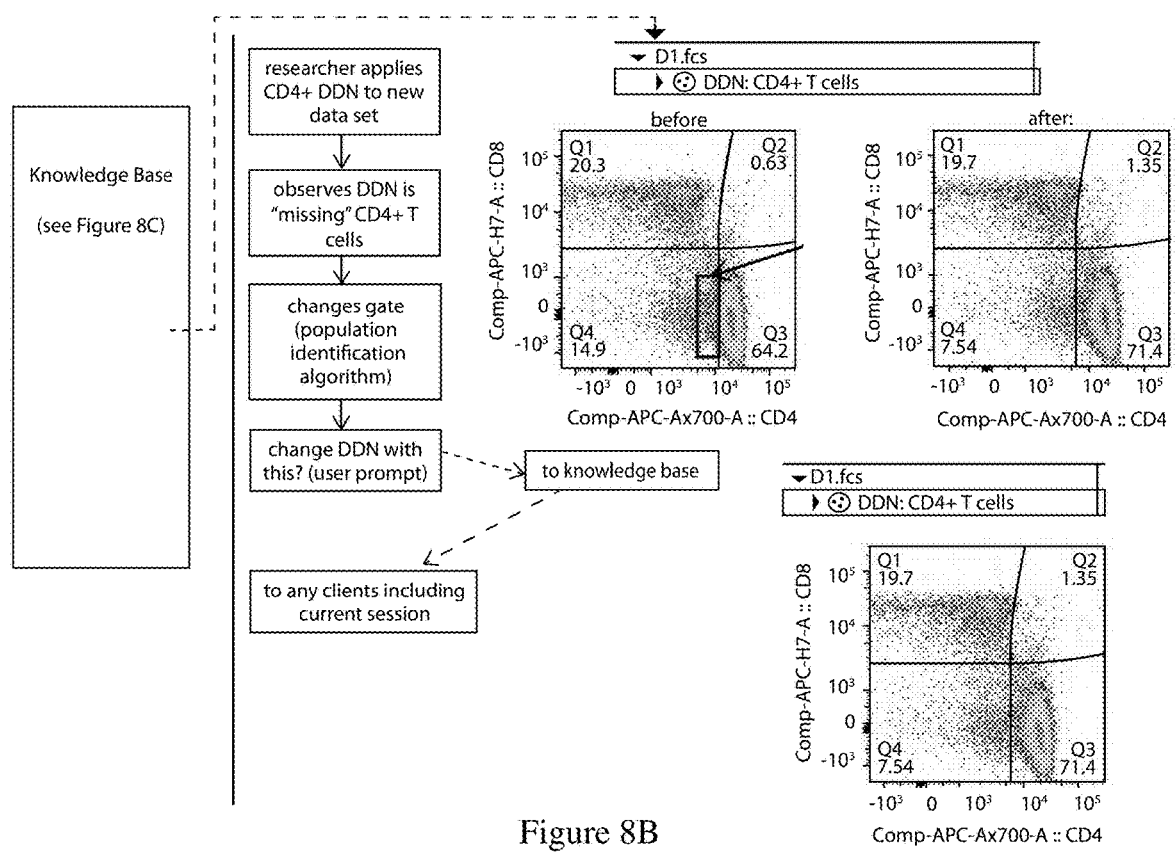

FIG. 8B shows an example as to how an expert could train a DDN. In this example, an expert may notice that a wider CD4 gate produces better analysis results. The expert may then widen the CD4 gate definition in his DDN using a user interface on a computer, which is performed by examining the CD4 populations in an expert, and editing a range gate to include more CD4+ cells in an analysis. After adjusting the DDN, the adjusted DDN gets saved in a database. An analyst may invoke the adjusted DDN without knowing that the DDN has a different CD4 gate definition. By invoking the adjusted DDN, the entire analysis flow defined by the adjusted DDN will occur in a single session of the analysis software. The adjusted DDN may generate results according to the adjusted method. Of the many benefits of this method, a substantial benefit is knowing that the adjusted analysis method is completely validated by an expert even though the analyst performed no different actions.

As another benefit, DDNs may be shared among groups or individuals. An expert in T-cells may retrieve a DDN created and optimized by an expert in NK cells to run an analysis on NK cells. Thus, expertise may be shared among experts, and experiments may be run efficiently on numerous phenotypes.

One of the main benefits of the active nodes is that the nodes are divorced from a particular data set and are data-driven. Because data drives the analysis flow, the types of analyses that become available will be different depending on the selection of input data. In other words, what the DDN can calculate and execute depends on the input data. Generally, the input data is a set of events representing scientific data, or a set of files with an implicit sense of equivalency. For example, the input data may be a CD3 measurement captured across multiple time points. As another example, input data may be raw data captured by the acquisition instrument. In yet another example, the input data may be resultant data generated by the analysis software or an external algorithm.

The metadata of a DDN may also specify whether to apply a constraint, branching, a decision tree, self-optimize, or iterate in real-time, which is specified by the user and stored as DDN execution parameters. The input analysis step may occur numerous times as the DDN receives resulting data fed back after an analysis step. Whether to branch, apply a constraint, apply a decision tree, etc. may be set within the metadata of the DDN or the satisfaction variables.

When the DDN applies a constraint, the DDN narrows the scope of the data. For example, if the input data to be narrowed was a single parameter distribution, a constraint could be a range, such as events ranging from 1 to 100. By narrowing the range, the DDN can exclude cells in extreme bins, which may be debris or add significant noise. Another application of a constraint in the context of a DDN would be removing noise to calculate the frequency of a subset or a ratio of two phenotypes, such as low white blood cell counts or HIV T-cell inversion, wherein the ratio of T-cell types in a patient "inverts". For example, the constraint may be applied by setting the operational variables to perform calculations on only the constrained subset of data.

When a DDN applies branching, the DDN generates a point in the workflow where a result will affect a subsequent execution step. As a simple example, if the DDN is attempting to find a CD3+ subset, but the DDN determines that there are no CD3+ events, that information can be used in-process and thus redirect downstream analysis adaptively. In this example, the DDN may apply a population identification algorithm to search for CD3+ cells. The DDN may receive the cluster population results identifying that no CD3+ cells were found. The DDN may analyze the results of the population identification algorithm, which represents the feedback loop of FIG. 5, and determine that the step of generating a report on CD3+ cells would be useless. Therefore, the DDN may instead request the population identification algorithm to identify a new population. In the HIV inversion example discussed above, if a DDN detects an HIV inversion situation using the metadata loaded by the DDN, the DDN may instruct the analysis software to perform a more in-depth report of T-cell numbers or report that the T-cell number was in the normal range. The use of a branching statement alters the in-session processing, which allows both leveraging adaptive execution and in-memory data. The operational variables may specify this type of branching during the completion phase. Alternatively, the metadata may include inherent branching that changes the specified calculation or algorithm applied to either the full set or subset of data.

Figure 9:
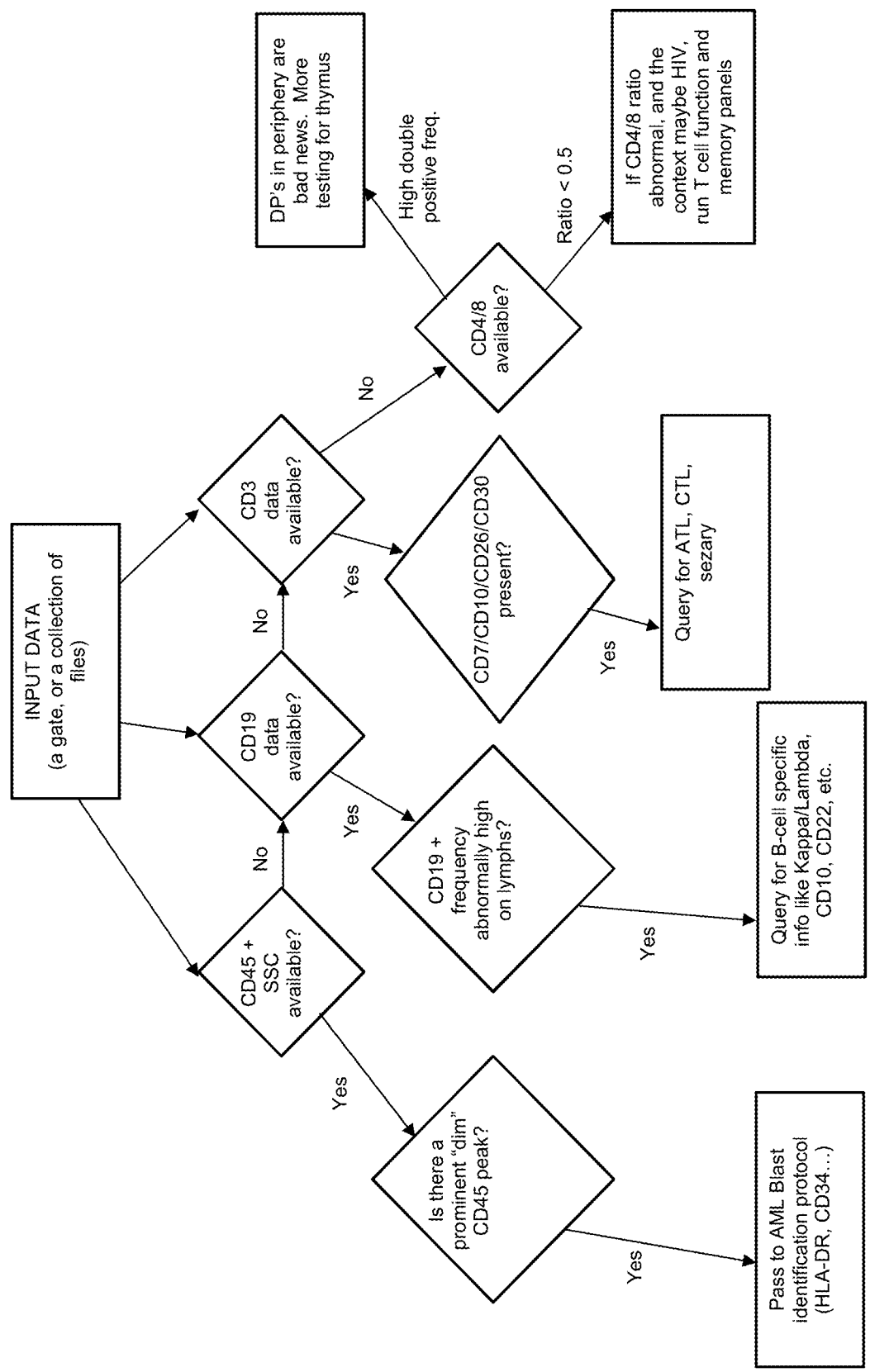
FIG. 9 illustrates a decision tree represented by a data discovery node.

The DDN may apply a decision tree, which is a representation of an entire processing flow to find a particular outcome. For example, FIG. 9 illustrates a decision tree example to find a particular population, which will involve event or dimensionality reduction. For some context regarding FIG. 9, a number of specialized panels to detect specific types of abnormalities in a sample data set already exist. The combinations of specific phenotypes that these panels represent can be mined from data that contains the markers. The DDN can server as a container for this logic. This arrangement permits a jump from panel-based analysis to algorithmic analysis such that a point will be reached where panels will become largely unnecessary. Rather than testing multiple panels, one can include all of the relevant markers into one tube, which means that the sophisticated processing capabilities of the DDN can be used to navigate through the large number of data parameters arising out of such testing.

Referring to FIG. 9, the input data may be a gate or a collection of files. As can be seen from FIG. 9, the DDN may determine whether CD45+ SSC data is available. If yes, the DDN analyzes the data to determine whether there is a prominent "dim" CD45 peak. In order, the DDN executes the following comparisons and analysis:

a. The two branches in FIG. 9 illustrate the process of validation which the DDN performs, first to examine whether an analysis can be completed (comparison to DDN execution parameters—in this case, does the sample contain SSC and CD45 parameters?
 b. If so, then an expert gate from the knowledge base is applied to a population identified by the SSC and CD45 parameters.
 c. A peak finding (population identification) algorithm is executed examining the CD45 parameter only to see if there is a CD45 dim peak (relative to the CD45+ population already gated).
    i. If a peak exists, then another expert series of hierarchical gates is applied, in this case to identify acute monocytic leukemia (AML) blasts.
 d. Regardless, CD19+ cells are identified by the DDN-applied population definition compared to the knowledge base to examine whether a CD19+ frequency is abnormally high (greater than two standard deviations, as defined by the expert upon DDN creation) on lymphocytes. If the CD19 frequency is abnormally high on lymphocytes, the DDN will apply an analysis for B-cell specific information like Kappa/Lambda, CD10, CD22, etc.

In every case, the DDN performs validation (can an analysis be performed), executes a phase of analysis (e.g. apply these expert-defined geometric gates or perform peak finding) compares to a biological result, and can repeat. In this manner, the DDN leverages its 3 information types to direct the analysis.

As can be seen from the non-limiting example in FIG. 9, the DDN can change processing based on the results of a determination at each point in the decision tree. The change in processing can be represented by the DDN's metadata and the operational variables, upon user invocation, e.g. when validation criteria fail. Also in contrast to conventional methods, the decision tree shown in FIG. 9 removes subjective bias by a human because the DDN processes all these decisions and results in a single session of the analysis software.

A DDN may also use optimization techniques to refine a result over a number of analysis "passes". One example of optimization would cell cycle fitting analysis where the analysis software calculates an estimate of how many cells are in a phase of the cell division cycle. An accurate number of cells in a division cycle is best found iteratively to refine the number found in the calculation. Refinement and optimization calls for multiple passes, and the DDN allows for a user to set a limit on the number of "passes" necessary to calculate an accurate result. The limit may be a number of iterations or using a threshold delta, whereby an improvement in accuracy in the calculation must exceed an improvement threshold or the process ceases. The cell cycle fitting analysis could extend to population identification where the identification algorithms may iteratively phenotype until the identification technique no longer exceeds the improvement threshold delta. The processor may change the DDN metadata based on optimization techniques.

Furthermore, a DDN may use iteration to repeat a process while reducing dimensionality or parameter range after each step. For example, a DDN may find all the peaks (maxima) in a distribution of data by analyzing starting from the minimum or maximum of the data range. Once the first peak is found, the DDN removes the peak from the data set so that the DDN can find more peaks, such as the second-from maximum peak, etc. Eventually, only one peak will remain, and after the DDN has found the last peak, the iteration stops. Iteration may be defined by the iteration variable included within the satisfaction variables.

Finally, a DDN may leverage training and knowledge learned from other similar DDNs. When a DDN is created by an expert, the DDN is configured to query a database for similar DDN data structures. The DDN may conduct this query by searching for similar names or similar items in its metadata. For example, if the DDN has meta-information identifying it as a CD4 identification node, the DDN may search for other DDNs saved in a DDN database having similar or identical metadata. The DDN may find similar DDNs through any semantic method. Upon finding similar DDNs, a newly trained DDN may gain information from the similar DDNs saved in the database that will allow the DDN to receive the knowledge and training gained by previously created DDNs. For example, a newly created DDN may find that a similar DDN has expertly defined geometric gates, or minimum/maximum ranges of a gate, percentiles for a gate, or mathematical relationships that help in generating clinically meaningful results. Each DDN may communicate to other DDN data structures the number of times it has been applied to data. As mentioned above, the more a DDN is applied to acquired data, the better the results are that the DDN generates. So, DDNs having been applied to more data may communicate to other, similar DDN data structures the ranges, percentiles, gates, mathematical relationships, parameter pruning, or any other important knowledge so that similar data structures may leverage the training of "older" DDNs. DDNs learn through invoking and also through communication with other similar DDN data structures in the database, thus leveraging a network of experts and iterative experimentation to yield an optimal e.g. population identification. In yet another example, a DDN may change the way or suggest a change to the way that data is collected by an acquisition instrument.

The DDN operates in memory of the computer and on input data stored in memory. When a user gestures to use a DDN, the DDN gathers the necessary input data into memory and performs data processing on the input data within the memory. Data may be reduced and pruned as the DDN iterates, applies constraints, makes decisions, branches or optimizes. As the DDN gains more intelligence, the DDN may perform initial pre-processing on the input data so that the amount of data stored in memory is minimized. By pre-processing the data, which occurs at the meta-data level, the performance of the computer increases as the DDN continues to train. Furthermore, by removing the subjectively biased steps of manual, geometric gating, results are presented to a user faster than previous experimentation methods. The acquisition computer, analysis computer, or the server may perform additional processing to perform all the features of the DDN, but efficiency is increased with the use of a DDN.

The DDN may also leverage table editors or layout editors contained within the analysis software for presenting results to the user. In some contexts, a DDN may encapsulate an entire analysis flow such that a user, such as an analyst, could simply invoke a DDN and without any other steps be presented with experiment results through the analysis software. In this way, the DDN could contain an entire experiment.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A computer program product for processing scientific data according to a model that is independent of any specific data set, the computer program product comprising:
a data discovery node data structure resident on a non-transitory computer-readable storage medium, the data discovery node data structure comprising (1) a specification of scientific data to be subjected to an iterative scientific data analysis, (2) a specification of an output format for the iterative scientific data analysis, and (3) a specification of a plurality of operational variables for controlling the iterative scientific data analysis, the specified operational variables comprising (i) a specification of an algorithm to be performed on the specified scientific data as part of the iterative scientific data analysis, (ii) a specification of metadata, the specified metadata configured to define conditions under which the specified algorithm will be applied to the specified scientific data, and (iii) a specification of a satisfaction variable, the specified satisfaction variable configured to control how many iterations are performed as part of the iterative scientific data analysis; and
a plurality of processor-executable instructions that are resident on a non-transitory computer-readable storage medium, wherein the instructions are configured, upon execution by a processor of a computer, to cause the computer to: read and invoke the data discovery data structure to perform the iterative scientific data analysis on a specific data set corresponding to the specified scientific data according to the specified operational variables, determine whether the metadata meets a metadata rule criteria specified by one of the plurality of operational variables, and generate a result in the specified output format,
wherein the step of determining whether the metadata meets a metadata rule criteria comprises testing the metadata against the metadata rule criteria according to a mode selected from the group consisting of a loose mode, a moderate mode, and a strict mode,
wherein the loose mode specifies the metadata has no requirements to meet the metadata rule criteria,
wherein the moderate mode specifies that the metadata must meet a number of criteria of the metadata rule criteria over a user-set threshold, and
wherein the strict mode specifies that the metadata must meet all criteria of the metadata rule criteria.

2. The computer program product of claim 1 wherein the instructions are further configured, upon execution by the processor, to cause the computer, as part of the read and invocation operations, to:
load the specified operational variables into memory;
test the loaded metadata against the specific data set;
determine a specified algorithm to be performed on the specific data set based on the metadata test operation;
apply the determined algorithm to the specified data set to produce a data analysis result;
create a temporary data object in memory that stores the result and a state for the iterative scientific data analysis;
determine whether another iteration of the iterative scientific data analysis is needed based on the loaded satisfaction variable;
in response to a determination that another iteration of the iterative scientific data analysis is needed, (1) repeat the metadata test operation, the specified algorithm determination, the algorithm application operation, and the another iteration determination operation until a determination is made that the loaded satisfaction variable has been satisfied, and (2) update the temporary data object based on the repeated algorithm application operation; and in response to a determination that another iteration of the scientific data analysis is not needed, write a result of the iterative scientific data analysis into a workspace in accordance with the specified output format.

3. The computer program product of claim 1 further comprising a plurality of the data discovery node data structures resident on the non-transitory computer-readable storage medium, wherein a plurality of the data discovery node data structures comprise different specifications relative to each other, and wherein the instructions are further configured, upon execution by the processor, to cause the computer to:

select a data discovery node data structure from among the plurality of data discovery node data structures in response to user input; and perform the read and invocation operations on the selected data discovery node data structure.

4. The computer program product of claim 3 wherein the instructions are further configured, upon execution by the processor, to cause the computer to:

define at least one of the specified operational variables for the selected data discovery node data structure in response to user input.

5. The computer program product of claim 1 wherein the specified algorithm comprises an external algorithm, and wherein the instructions are further configured, upon execution by the processor, to cause the computer to:

invoke the external algorithm via an external algorithm plug-in interface framework.

6. The computer program product of claim 1 wherein the specified algorithm is executed by a remote computer, and wherein the instructions are further configured, upon execution by the processor, to cause the computer to:

invoke the specified algorithm via a remote computer plug-in interface framework.

7. The computer program product of claim 1 wherein the scientific data comprises cell data from an experiment.

8. The computer program product of claim 7 wherein the cell data comprises single cell data acquired by a flow cytometer.

9. The computer program product of claim 7 wherein the specified algorithm comprises a population identification algorithm.

10. The computer program product of claim 7 wherein the specified algorithm comprises a geometric gating algorithm.

11. A method for analyzing scientific data comprising:

applying a data discovery node data structure to a data file, the data file comprising scientific data collected by an acquisition instrument, the data file having metadata associated therewith, wherein the applying step comprises:

loading a plurality of operational variables associated with the data discovery node and the metadata associated with the data file into memory;

determining whether the metadata meets a metadata rule criteria specified by one of the plurality of operational variables; and in response to a determination that the metadata meets the metadata rule criteria:

loading the scientific data associated with the data file into memory;

executing a first analysis algorithm on the scientific data associated with the data file, wherein one of the plurality of operational variables specifies the first analysis algorithm;

creating a temporary data object that defines a satisfaction variable;

determining whether the temporary data object's satisfaction variable satisfies a satisfaction threshold specified by one of the plurality of operational variables; and in response to a determination that the temporary data object's satisfaction variable does not satisfy the satisfaction threshold, (1) executing either the first analysis algorithm or a second analysis algorithm on a full set or a subset of the scientific data associated with the data file, wherein one of the plurality of operational variables defines whether to apply the first analysis algorithm or the second analysis algorithm to the full set or the subset of the raw data, and (2) updating the temporary data object based on the executing of the first analysis algorithm or the second analysis algorithm; and repeatedly performing the steps of (1) determining whether the temporary data object's satisfaction variable satisfies the satisfaction threshold, (2) executing either the first analysis algorithm or the second analysis algorithm, and (3) updating the temporary data object until the updated temporary data object's satisfaction variable satisfies the satisfaction threshold, wherein the step of determining whether the metadata meets a metadata rule criteria comprises testing the metadata against the metadata rule criteria according to a mode selected from the group consisting of a loose mode, a moderate mode, and a strict mode, wherein the loose mode specifies the metadata has no requirements to meet the metadata rule criteria, wherein the moderate mode specifies that the metadata must meet a number of criteria of the metadata rule criteria over a user-set threshold, wherein the strict mode specifies that the metadata must meet all criteria of the metadata rule criteria, and wherein the method steps are performed by a processor.

12. The method of claim 11 wherein the data discovery node is a pre-defined data structure saved in a database.

13. The method of claim 11 wherein the data discovery node is a newly defined data structure created by a user.

14. The method of claim 13 further comprising storing the newly defined data discovery node in a database for future use.

15. The method of claim 14 further comprising:

the processor searching for a similar data discovery node in the database; and analyzing parameters of the similar data discovery node and comparing the parameters of the similar data discovery node with the parameters of the data discovery node.

16. The method of claim 11 wherein the operational variables comprise a plurality of acquisition instrument parameters, feature variables, iteration variables, and range variables.

17. A computer program product comprising:

a plurality of processor-executable instructions that are resident on a non-transitory computer-readable storage medium, wherein the instructions are configured for execution by the processor to analyze scientific data by causing the computer to:

apply a node data structure to a data file, the data file comprising scientific data collected by an acquisition instrument, the data file having metadata associated therewith, wherein the apply operation is configured to:
load a plurality of operational variables associated with the data discovery node and the metadata associated with the data file into memory;
determine whether the metadata meets a metadata rule criteria specified by one of the plurality of operational variables; and
in response to a determination that the metadata meets the metadata rule criteria:
  load the scientific data associated with the data file into memory;
  execute a first analysis algorithm on the scientific data associated with the data file, wherein one of the plurality of operational variables specifies the first analysis algorithm;
  create a temporary data object that defines a satisfaction variable;
  determine whether the temporary data object's satisfaction variable satisfies a satisfaction threshold specified by one of the plurality of operational variables; and
  in response to a determination that the temporary data object's satisfaction variable does not satisfy the satisfaction threshold, (1) execute either the first analysis algorithm or a second analysis algorithm on a full set or a subset of the scientific data associated with the data file, wherein one of the plurality of operational variables defines whether to apply the first analysis algorithm or the second analysis algorithm to the full set or the subset of the raw data, and (2) update the temporary data object based on the executing of the first analysis algorithm or the second analysis algorithm; and
  repeatedly perform the (1) determination operation as whether the temporary data object's satisfaction variable satisfies the satisfaction threshold, (2) the first analysis algorithm or the second analysis algorithm execution operation, and (3) the update operation until the updated temporary data object's satisfaction variable satisfies the satisfaction threshold,
wherein the step of determining whether the metadata meets a metadata rule criteria comprises testing the metadata against the metadata rule criteria according to a mode selected from the group consisting of a loose mode, a moderate mode, and a strict mode,
wherein the loose mode specifies the metadata has no requirements to meet the metadata rule criteria,
wherein the moderate mode specifies that the metadata must meet a number of criteria of the metadata rule criteria over a user-set threshold, and
wherein the strict mode specifies that the metadata must meet all criteria of the metadata rule criteria.

18. A method for analyzing scientific data comprising:
receiving a specification of a plurality of operational variables, wherein the specification comprises (1) a specification of a satisfaction criteria, (2) a specification of a first analysis algorithm, (3) a specification of a second analysis algorithm, and (4) a specification of metadata specifying conditions under which the first and second analysis algorithms are to be applied to the scientific data;
executing the first analysis algorithm on at least a portion of the scientific data based on the operational variable that specifies the first analysis algorithm and the operational variable that specifies the conditions under which the first analysis algorithm is to be applied to the scientific data; and
repeatedly executing the first analysis algorithm or a second analysis algorithm on at least a portion of the scientific data based on the results of the executing step and the operational variables until the satisfaction criteria is met; and
determining whether the metadata meets a metadata rule criteria specified by one of the plurality of operational variables,
wherein the step of determining whether the metadata meets a metadata rule criteria comprises testing the metadata against the metadata rule criteria according to a mode selected from the group consisting of a loose mode, a moderate mode, and a strict mode,
wherein the loose mode specifies the metadata has no requirements to meet the metadata rule criteria,
wherein the moderate mode specifies that the metadata must meet a number of criteria of the metadata rule criteria over a user-set threshold,
wherein the strict mode specifies that the metadata must meet all criteria of the metadata rule criteria, and
wherein the method steps are performed by a processor.

19. The method of any of claim 18 wherein one of the plurality of operational variables specifies whether to analyze the scientific data or the subset of scientific data.

20. The method of claim 18 further comprising the processor creating a temporary object comprising a satisfaction value, wherein the processor updates the satisfaction value after the processor executes an analysis algorithm on data; and
the processor comparing the value of the satisfaction value to the satisfaction criteria to determine whether the satisfaction criteria is met.

21. The method of claim 18 wherein the processor determines whether to execute the first or the second analysis algorithm based on results generated by the processor executing the first analysis algorithm on the scientific data.

22. The method of claim 18 wherein the processor determines whether to analyze the scientific data or the subset of scientific data based on results generated by the processor executing the first analysis algorithm on the scientific data.

23. The method of claim 18 wherein at least one of the specified analysis algorithms comprises an external analysis algorithm.

24. A computer program product comprising:
a plurality of processor-executable instructions that are resident on a non-transitory computer-readable storage medium, wherein the instructions are configured for execution by the processor to analyze scientific data by causing the computer to:
receive a specification of a plurality of operational variables, wherein the specification comprises (1) a specification of a satisfaction criteria, (2) a specification of a first analysis algorithm, (3) a specification of a second analysis algorithm, and (4) a specification of metadata specifying conditions under which the first and second analysis algorithms are to be applied to the scientific data;
execute the first analysis algorithm on at least a portion of the scientific data based on the operational variable that specifies the first analysis algorithm and the operational variable that specifies the conditions under which the first analysis algorithm is to be applied to the scientific data; and repeatedly execute the first analysis algorithm or a second analysis algorithm on at least a portion of the scientific data based on the results of the executing step and the operational variables until the satisfaction criteria is met;

determining whether the metadata meets a metadata rule criteria specified by one of the plurality of operational variables, wherein the step of determining whether the metadata meets a metadata rule criteria comprises testing the metadata against the metadata rule criteria according to a mode selected from the group consisting of a loose mode, a moderate mode, and a strict mode, wherein the loose mode specifies the metadata has no requirements to meet the metadata rule criteria, wherein the moderate mode specifies that the metadata must meet a number of criteria of the metadata rule criteria over a user-set threshold, and wherein the strict mode specifies that the metadata must meet all criteria of the metadata rule criteria.

* * * * *